(12) United States Patent
Carr et al.

(10) Patent No.: US 7,087,724 B2
(45) Date of Patent: Aug. 8, 2006

(54) CARRIER MOLECULES

(75) Inventors: Francis J. Carr, Aberdeen (GB); Anita A. Hamilton, Aberdeen (GB)

(73) Assignee: Agen Biomedical Ltd, Brisbane (AU)

( * ) Notice: Subject to any disclaimer, the term of this patent is extended or adjusted under 35 U.S.C. 154(b) by 200 days.

(21) Appl. No.: 10/184,300

(22) Filed: Jun. 26, 2002

(65) Prior Publication Data
US 2003/0124056 A1 Jul. 3, 2003

Related U.S. Application Data

(60) Provisional application No. 60/300,947, filed on Jun. 27, 2001, provisional application No. 60/301,154, filed on Jun. 26, 2001.

(51) Int. Cl.
C12P 21/08 (2006.01)
C07K 16/00 (2006.01)

(52) U.S. Cl. .................... 530/387.3; 530/391.3
(58) Field of Classification Search ............. 530/387.3, 530/391.3
See application file for complete search history.

(56) References Cited

U.S. PATENT DOCUMENTS

| | | | |
|---|---|---|---|
| 4,758,524 A | 7/1988 | Bundesen et al. | |
| 4,946,778 A | 8/1990 | Ladner et al. | |
| 5,091,513 A | 2/1992 | Huston et al. | |
| 5,837,821 A | 11/1998 | Wu | |
| 6,056,957 A | 5/2000 | Chou et al. | |
| 6,132,719 A | 10/2000 | Kohno et al. | |
| 6,180,370 B1 | 1/2001 | Queen et al. | |
| 6,180,377 B1 | 1/2001 | Morgan et al. | |
| 6,632,927 B1 * | 10/2003 | Adair et al. | |

FOREIGN PATENT DOCUMENTS

| | | |
|---|---|---|
| EP | 0 239 400 | 9/1987 |
| EP | 0 347 933 | 12/1989 |
| WO | WO 91/02547 | 3/1991 |
| WO | WO 94/09034 | 4/1994 |
| WO | WO 98/52976 | 11/1998 |

OTHER PUBLICATIONS

Lewis Securities Ltd. http://www.comupdate.com.au/issues/dec98.htm, pp. 1-4, Dec. 1998.*
Bautovich G, et al. Detection of deep venous thrombi and pulmonary embolus with technetium-99m-DD-3B6/22 anti-fibrin monoclonal antibody Fab' fragment. J Nucl Med. Feb. 1994;35(2):195-202.*
Biovation Therapeutic Antibodies J591 and 3B6 Antibodies. http://www.biovation.co.uk/pages/products/1/. pp. 1, 2004.*
Rudikoff et al. Single amino acid substitution altering antigen-binding specificity. Proc Natl Acad Sci U S A. Mar. 1982;79(6):1979-83.*
Panka et al. Variable region framework differences result in decreased or increased affinity of variant anti-digoxin antibodies. Proc Natl Acad Sci U S A. May 1988;85(9):3080-4.*
Attwood TK. Genomics. The Babel of bioformatics. Science. Oct. 2000:290(5491):471-3.*
Skolnick et al. From genes to protein structure and function: novel applications of computational approaches in the genomic era. Trends Biotechnol. Jan. 2000;18(1):34-9.*
Adams, G.P. et al. (Sep. 1, 1993). "Highly Specific *in Vivo* tumor Targeting by Monovalent and Divalent Forms of 741F8 Anti-c-*erb*B-2 Single-Chain Fv," *Cancer Research* 53:4026-4034.
AGEN Media Release. (Feb. 1, 2001) "Major Development in Agen/BII Blood Clot Imaging Technology," AGEN Biomedical Limited—Media Release located at <http://web.archive.org/web/2001602122513/www.agen.com.au/news/mr011.htm> visited on Sep. 7, 2002 (2 pages).
Altschul, S.F. et al. (1997). "Gapped BLAST and PSI-BLAST: a new generation of protein database search programs," *Nucl. Acids Res.* 25(17):3389-3402.
Ausubel, F.M. et al. eds. (2001). "Chapter 15: Polymerase Chain Reaction" In *Current Protocols in Molecular Biology* John Wiley & Sons Inc., vol. 3, Supplementa 56, pp. 1-2, 15.0.1-15.6.9.

(Continued)

*Primary Examiner*—Maher Haddad
(74) *Attorney, Agent, or Firm*—Robins & Pasternak LLP

(57) ABSTRACT

The present invention relates generally to carrier molecules derived from one animal or avian species or strains and which are substantially non-immunogenic when exposed to an immune system from a species or strain of another animal or avian creature. More particularly, the present invention provides deimmunized immunointeractive molecules and even more particular deimmunized antibodies for use in diagnostic and therapeutic applications.

8 Claims, 7 Drawing Sheets

OTHER PUBLICATIONS

Figure 1A:
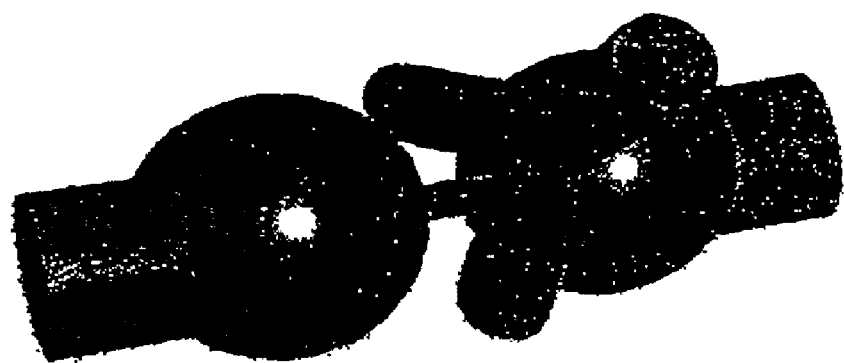

Bautovich, G. et al. (Feb. 1994). "Detection of Deep Venous Thrombi and Pulmonary Embolus with Technetium-99m-DD-3B6/22 Anti-fibrin Monoclonal Antibody Fab' Fragment," *Journal of Nuclear Medicine* 35(2):195-202.

Bechtol, K.B. (1981). "Quantitative Absorption/Blocking Assay," *In Monoclonal Antibodies Hybridomas:A New Dimension in Biological Analyses* Plenum Press, New York, New York, pp. 383-384.

Bechtol, K.B. (1981). "Radioimmunoassay," *In Monoclonal Antibodies Hybridomas:A New Dimension in Biological Analyses* Plenum Press, New York, New York, pp. 381-382.

Bonner, T.I. et al. (1973). "Reduction in the Rate of DNA Reassociation by Sequence Divergence," *J. Mol. Biol.* 81(2):123-135.

Budzynski. A. Z. et al. (1979). "Antigenic Markers on Fragment DD, A Unique Plasmic Derivative of Human Crosslinked Fibrin," *Blood* 54(4):794-804.

Chothia, C. and Lesk, A.M. (1987). "Canonical Structures for the Hypervariable Regions of Immunoglobulins," *J. Mol. Biol*, 196:901-917.

Chothia, C. et al. (1992). "Structural Repertoire of the Human $V_H$ Segments," *J. Mol. Biol.* 227:799-817.

Coligan et al., eds. (1991-1997). in *Current Protocols in Immunology*, vol. 1, John Wiley & Sons, Inc., USA, Supplement 54, Table of Contents pp. 1-10.

Cumber, A.J. et al. (1992). "Comparative Stabilities in Vitro and in Vivo of a Recombinant Mouse Antibody FvCys Fragment and bisFvCys Conjugate," *J. Immunol.* 149(1):120-126.

Dauherty, B.L. et al. (1991). "Polymerase chain reaction facilitates the cloning, CDR-grating, and rapid expression of a murine nonoclonal antibody directed against the CD18 component of leukocyte integrins," *Nucleic Acids Research* 19(9):2471-2476.

Davies, J. and Riechmann, L. (1994). "'Camelising' human antibody fragments:NMR studies on VH domains," *FEBS Lett*. 339:285-290.

Foung, S.K.H. et al. (1986). "Generation of Human Monoclonal Antibodies by Fusion of EBV-Activated B Cells to a Human-Mouse Hybridoma," Chapter 13 In *Methods in Enzymology—vol. 121, Immunochemical Techniques, Part I, Hybridoma Technology and Monoclonal Antibodies*, Langone and Vunakis Editors, Academic Press, Inc. New York, pp. 168-174.

Gefter, M.L. et al. (1977). "A Simple Method for Polyethylene Glycol-Promoted Hybridization of Mouse Myeloma Cells," *Somatic Cell Genet*. 3(2):231-236.

Glockshuber, R. et al. (1990). "A Comparison of Strategies To Stabilize Immunoglobulin $F_v$- Fragments" *Biochem.* 29:1362-1367.

Graeff, H and Halfer, R. (1982). "Detection and Relevance of Cross-linked Fibrin Derivatives in Blood," *Seminars in Thrombosis and Hemostatis* 8(1):57-68.

Hamers-Casterman, C. et al. (1993). "Naturally occurring antibodies devoid of light chains," *Nature* 363:446-448.

Jonak, Z.L. (1981). "*Peroxidase-Conjugated Antiglobulin Method for Visual Detection of Cell-Surface Antigens*," In *Monoclonal Antibodies Hybridomas:A Dimension in Biological Analyses* Plenum Press, New York, New York, pp. 378-380.

Jones, P.T. et al. (1986). "Replacing the complementarity-determining regions in a human antibody with those from a mouse," *Nature* 321:522-525.

Kabat, E.A. et al. (1991). *Sequences of Proteins of Immunological Interest*, U.S. Department of Health and Human Services, 5th edition, NIH Publication No. 91-3242, pp. iii-xi. (Table of Contents).

Kennett, R.H. (1981). "Enzyme-Linked antibody Assay with Cells Attached to Polyvinyl Chloride Plates," *In Monoclonal Antibodies Hybridomas:A Dimension in Biological Analyses* Plenum Press, New York, pp. 376-377.

Kohler, G. and Milstein, C. (1975). "Continuous cultures of fused cells secreting antibody of predefined specificity," *Nature* 256:495-497.

Kohler, G. and Milstein, C. (1976). "Derivation of specific antibody-producing tissue culture and tumor lines by cell fusion," *Eur. J. Immunol.* 6(7):511-519.

Kostelny, S.A. et al. (1992). "Formation of a Bispecific Antibody by the Use of Leucine Zippers," *J. Immunol.* 148(5):1547-1553.

Krebber, A. et al. (1997). "Reliable cloning of functional antibody variable domains from hybridomas and spleen cell repertoires employing a reengineered phage display system," *J. Immunol. Methods* 201(1):35-55.

Ku, J. and Schutz, P.G. (1995). "Alternate protein frameworks for molecular recogniton," *Proc. Natl. Acad. Sci. USA* 92:6552-6556.

Liu, A.Y. et al. (1987). "Chimeric mouse-human IgG1 antibody that can mediate lysis of cancer cells," *Proc. Natl. Acad. Sci. USA* 84:3439-3443.

Marmur, J. and Doty, P. (1962). "Determination of the Base Composition of Deoxyribonucleic Acid from its Thermal Denaturation Temperature," *J. Mol. Biol.* 5:109-118.

Orlandi, R. et al. (1989). "Cloning immunoglobulin variable domains for expression by the polymerase chain reaction," *Proc. Natl. Acad. Sci. USA* 86:3833-3837.

Pack, P. and Plünckthun, A. (1992). "Miniantibodies:Use of Amphipathic Helices To Produce Functional, Flexibly Linked Dimeric $F_v$ Fragments with High Avidity in *Escherichia coli*," *Biochem*. 31(6):1579-1584.

Plückthun, A. et al. (1996). "Producing Antibodies in *Escherichia coli*: from PCR to Fermentation," Chapter 10 *In Antibody engineering:A practical approach*. McCafferty,J. et al eds. Oxford University Press: Oxford. pp. 203-252.

Reiter, Y. et al. (1994) "Improved Binding and Antitumor Activity of a Recombinant Anti-erbB2 Immunotoxin by Disulfide Stabilization of the Fv Fragment," *J. Biol. Chem.* 269(28):18327-18331.

Reiter, Y. et al. (1994). "Antitumor Activity and Pharmacokinetics in Mice of a Recombinant Immunotoxin Containing a Disulfide-Stabilized Fv Fragment," *Cancer Res*. 54:2714-2718.

Reiter, Y. et al. (1994). "Stabilization of the Fv Fragments in Recombinant Immunotoxins by Disulfide Bonds Engineered into Conserved Framework Regions," *Biochem*. 33:5451-5459.

Riechmann, L. et al. (1988). "Reshaping human antibodies for therapy," *Nature* 332:323-327.

Roder, J.C. et al. (1986). "The EBV-Hybridoma Technique," Chapter 12 *In Methods in Enzymology*—vol. 121, Immunochemical Techniques, Part I, Hybridoma Technology and Monoclonal Antibodies, Langone and Vunakis Editors, Academic Press, Inc. New York, pp. 140-167.

Shulman, M. et al. (1978). "A better cell line for making hybridomas secreting specific antibodies," *Nature* 276:269-270.

Tempest, P.R. et al. (1991). "Reshaping a Human Monoclonal Antibody to Inhibit Human Respiratory Syncytial Virus Infection *In Vivo*," *Biotechnology* 9:266-271.

Trowbridge, I.S. (1978). "Interspecies Spleen-myeloma Hybrid Producing Monoclonal Antibodies Against Mouse Lymphocyte Surface Glycoprotein, T200," *J. Exp. Med.* 148(1):313-323.

Vandamme, A.M. et al. (1990). "Construction and Characterization of a Recombinant Murine Monoclonal Antibody Directed Against Human Fibrin Fragment-D-Dimer," *European Journal of Biochemistry* 192(3):767-775.

Vandamme, A.M. et al. (1992). "Characterization of a Recombinant Chimeric Plasminogen Activator Composed of a Fibrin Fragment-D-Dimer-Specific Humanized Monoclonal Antibody and a Truncated Single-Chain Urokinase," *European Journal of Biochemistry* 205(1):139-146.

Van Mourik, P. van and Zeijlemaker W.P. (1986). "Improved Hybridoma Technology:Spleen Cell Separation and Soluble Growth Factors," Chapter 14 *In Methods in Enzymology*—vol. 121, Immunochemical Techniques, Part I, Hybridoma Technology and Monoclonal Antibodies, Langone and Vunakis Editors, Academic Press, Inc. New York, pp. 174-183.

Verhoeyen, M. et al. (1998). "Reshaping Human antibodies:Grafting an Antilysozyme Activity," *Science* 239:1534-1536.

Volk, S.E. et al. (1982). "Monoclonal Antibodies to the Glycoprotein of Vesicular Stomatitis Virus:Comparative Neutralizing Activity," *J. Virol.* 42(1):220-227.

Ward, S.E. et al. (1989). "Binding activities of a repertoire of single immunoglobulin variable domains secreted from *Escherichia coli*," *Nature* 341:544-546.

Webber; K.O. et al. (1995). "Preparation and Characterization of a Disulfide-Stabilized Fv Fragment of the Anti-Tac Antibody:Comparison With Its Single Chain Analog," *Mol. Immunol.* 32(4):249-258.

Wilner, G.D. et al. (1982). "Monoclonal Antibodies to Fibrinogen:Modulation of Determinants Expressed in Fibrinogen by γ-Chain Cross-Linking," *Biochemistry* 21:2687-2692.

Winter, G. and Harris, W.J. (1993). "Humanized Antibodies," *Trends in Pharmacological Sciences* 14(5):139-143.

Winter, G. and Milstein, C. (1991). "Man-made antibodies," *Nature* 349:293-399.

Bulens et al., "Construction and Characterization of a Functional Chimeric Murine-Human Antibody Directed Against Human Fibrin Fragment-D Dimer" Eur. J. Biochem. 195:235-242 (1991).

Devine et al., "Monoclonal Antibody to Fibrin D-Dimer (DD-3B6) Recognizes an Epitope on the γChain of Fragment D" Amer. J. Clin. Pathol., 89(5):663-666 (1988).

Tymkewycz et al., "Screening for Fibrin Specific Monoclonal Antibodies: The Development of a New Procedure" Thrombosis and Haemostasis—© F.K. Schattauer Verlagsgesellschaft mbH (Stuttgart), 68(1):48-53 (1992).

Wylie et al., "Variable Immunoreactivity of D-Dimer Preparations for Monoclonal Antibody DD-3B6/22" Blood Coagulation and Fibrinolysis, 6:738-742 (1995).

"Therapeutic Proteins: Room for Improvement? A Novel, Highly Directed Approach has Been Developed to Overcome the Problems of Immunogenicity Associated With Therapeutic Proteins" innovations in Pharmaceutical Technology, pp. 79-85 (Jun. 2002).

"The Immunogenicity of Therapeutic Proteins" BioPharm, pp. 30-36 (Feb. 2002).

\* cited by examiner

X4,200 magnification

SEQUENCE LISTING

```
<160> NUMBER OF SEQ ID NOS: 12

<210> SEQ ID NO 1
<211> LENGTH: 118
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv5

<400> SEQUENCE: 1

Asp Val Gln Leu Lys Glu Ser Gly Pro Gly Leu Val Lys Pro Thr Gln
1               5                   10                  15

Thr Leu Thr Leu Thr Cys Thr Val Thr Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60

Thr Ser Arg Ile Ser Ile Ser Arg Asp Thr Ser Lys Asn Gln Phe Phe
65                  70                  75                  80

Leu Gln Leu Asn Ser Leu Thr Ser Glu Asp Thr Ala Thr Tyr Tyr Cys
                85                  90                  95

Ala Arg Glu Trp Phe Pro Tyr Tyr Phe Asp Tyr Trp Gly Gln Gly Thr
            100                 105                 110

Thr Leu Thr Val Ser Ser
        115

<210> SEQ ID NO 2
<211> LENGTH: 118
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv6

<400> SEQUENCE: 2

Asp Val Gln Leu Lys Glu Ser Gly Pro Gly Leu Val Lys Pro Thr Gln
1               5                   10                  15

Thr Leu Thr Leu Thr Cys Thr Val Thr Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Met Gly Tyr Ile Thr Tyr Ser Gly Thr Thr Ser Tyr Asn Pro Ser Leu
    50                  55                  60
```

```
Thr Ser Arg Ile Ser Ile Ser Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Arg Glu Trp Phe Pro Tyr Tyr Phe Asp Tyr Trp Gly Gln Gly Thr
            100                 105                 110

Thr Leu Thr Val Ser Ser
        115

<210> SEQ ID NO 3
<211> LENGTH: 118
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv7

<400> SEQUENCE: 3

Asp Val Gln Leu Lys Glu Ser Gly Pro Gly Leu Val Lys Pro Thr Gln
1               5                   10                  15

Thr Leu Thr Leu Thr Cys Thr Val Thr Gly Tyr Ser Ile Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Thr Thr Ser Tyr Asn Pro Ser Leu
        50                  55                  60

Thr Ser Arg Ile Ser Ile Ser Arg Asp Thr Ser Lys Asn Gln Phe Phe
65                  70                  75                  80

Leu Gln Leu Asn Ser Val Thr Ser Glu Asp Thr Ala Thr Tyr Tyr Cys
                85                  90                  95

Ala Arg Glu Trp Phe Pro Tyr Tyr Phe Asp Tyr Trp Gly Gln Gly Thr
            100                 105                 110

Thr Leu Thr Val Ser Ser
        115

<210> SEQ ID NO 4
<211> LENGTH: 107
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv1

<400> SEQUENCE: 4

Asp Ile Val Met Thr Gln Ser Gln Lys Ser Met Ser Thr Ser Val Gly
1               5                   10                  15

Asp Arg Val Ser Ile Ser Cys Lys Ala Ser Gln Asn Val Gly Thr Pro
                20                  25                  30

Val Ala Trp Tyr Gln Gln Lys Pro Glu Gln Ser Pro Lys Leu Leu Ile
            35                  40                  45

Tyr Ser Thr Ser Thr Arg Tyr Pro Gly Val Pro Asp Arg Phe Thr Gly
        50                  55                  60

Ser Gly Ser Gly Thr Asp Phe Thr Leu Thr Ile Ser Asn Leu Gln Ala
65                  70                  75                  80

Glu Asp Val Ala Asp Tyr Phe Cys Gln Gln Tyr Ser Leu Tyr Pro Leu
                85                  90                  95

Thr Phe Gly Ala Gly Thr Lys Val Glu Leu Lys
```

<210> SEQ ID NO 5
<211> LENGTH: 107
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv4

<400> SEQUENCE: 5

Asp Ile Val Met Thr Gln Ser Gln Lys Ser Met Ser Thr Ser Val Gly
1               5                   10                  15

Asp Arg Val Ser Ile Ser Cys Lys Ala Ser Gln Asn Val Gly Thr Pro
            20                  25                  30

Val Ala Trp Tyr Gln Gln Lys Pro Glu Gln Ser Pro Lys Leu Leu Ile
        35                  40                  45

Tyr Ser Thr Ser Thr Arg Tyr Pro Gly Val Pro Asp Arg Phe Thr Gly
50                  55                  60

Ser Gly Ser Gly Thr Asp Phe Thr Leu Thr Ile Ser Asn Leu Gln Ser
65                  70                  75                  80

Glu Asp Leu Ala Asp Tyr Phe Cys Gln Gln Tyr Ser Leu Tyr Pro Leu
                85                  90                  95

Thr Phe Gly Ala Gly Thr Lys Val Glu Leu Lys
            100                 105

<210> SEQ ID NO 6
<211> LENGTH: 107
<212> TYPE: PRT
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv7

<400> SEQUENCE: 6

Asp Ile Val Met Thr Gln Ser Gln Lys Ser Met Ser Thr Ser Val Gly
1               5                   10                  15

Asp Arg Val Ser Ile Ser Cys Lys Ala Ser Gln Asn Val Gly Thr Pro
            20                  25                  30

Val Ala Trp Tyr Gln Gln Lys Pro Glu Gln Ser Pro Lys Leu Leu Ile
        35                  40                  45

Tyr Ser Thr Ser Thr Arg Tyr Pro Gly Val Pro Asp Arg Phe Thr Gly
50                  55                  60

Ser Gly Ser Gly Thr Asp Phe Thr Leu Thr Ile Ser Asn Leu Gln Ala
65                  70                  75                  80

Glu Asp Val Ala Asp Tyr Phe Cys Gln Gln Tyr Ser Leu Tyr Pro Leu
                85                  90                  95

Thr Phe Gly Ala Gly Thr Lys Leu Glu Leu Lys
            100                 105

<210> SEQ ID NO 7
<211> LENGTH: 354
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv5

<400> SEQUENCE: 7

```
gatgtgcagc ttaaggagtc gggacctggc ctggttaaac ctactcagac tctgaccctc    60
acctgcactg tcactggcta ctcaatcacc agtgattatg cctggaactg gatacggcag   120
ccaccaggaa agggactgga gtggatgggc tacataacct acagtggtac cactagctac   180
aacccatctc tcacaagtcg aatctctatc tctcgcgaca catccaagaa ccagttcttc   240
ctgcagttga attctctgac ttctgaggac acagccacat attactgtgc aagagagtgg   300
tttccttact actttgacta ctggggccaa ggcaccactc tcacagtctc ttca         354
```

<210> SEQ ID NO 8
<211> LENGTH: 354
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv6

<400> SEQUENCE: 8

```
gatgtgcagc ttaaggagtc gggacctggc ctggttaaac ctactcagac tctgaccctc    60
acctgcactg tcactggcta ctcaatcacc agtgattatg cctggaactg gatacggcag   120
ccaccaggaa agggactgga gtggatgggc tacataacct acagtggtac cactagctac   180
aacccatctc tcacaagtcg aatctctatc tctcgcgaca catccaagaa ccagttcttc   240
ctgcagttga attctgtgac ttctgaggac acagccacat attactgtgc aagagagtgg   300
tttccttact actttgacta ctggggccaa ggcaccactc tcacagtctc ttca         354
```

<210> SEQ ID NO 9
<211> LENGTH: 354
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVHv7

<400> SEQUENCE: 9

```
gatgtgcagc ttaaggagtc gggacctggc ctggttaaac ctactcagac tctgaccctc    60
acctgcactg tcactggcta ctcaatcacc agtgattatg cctggaactg gatacggcag   120
tttccaggaa acaaactgga gtggatgggc tacataacct acagtggtac cactagctac   180
aacccatctc tcacaagtcg aatctctatc tctcgcgaca catccaagaa ccagttcttc   240
ctgcagttga attctgtgac ttctgaggac acagccacat attactgtgc aagagagtgg   300
tttccttact actttgacta ctggggccaa ggcaccactc tcacagtctc ttca         354
```

<210> SEQ ID NO 10
<211> LENGTH: 321
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv1

<400> SEQUENCE: 10

```
gacattgtga tgacccagtc tcaaaaatcc atgtccacat cagtaggaga cagggtcagc    60
atctcctgca aggccagtca gaatgtgggt actcctgtag cctggtatca gcagaaacca   120
gaacaatctc ctaaacttct gatttactcg acatccactg gtaccctgg agtccctgat    180
```

-continued

```
cgcttcactg gcagtggatc tgggacagat ttcactctca ccatcagcaa tctgcaggct    240
gaagacgtgg cagattattt ctgccagcaa tatagcctct atcctctcac gttcggtgct    300
gggaccaagg tggagctgaa a                                              321

<210> SEQ ID NO 11
<211> LENGTH: 321
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv4

<400> SEQUENCE: 11
gacattgtga tgacccagtc tcaaaaatcc atgtccacat cagtaggaga cagggtcagc     60
atctcctgca aggccagtca gaatgtgggt actcctgtag cctggtatca gcagaaacca    120
gaacaatctc ctaaacttct gatttactcg acatccactc ggtaccctgg agtccctgat    180
cgcttcactg gcagtggatc tgggacagat ttcactctca ccatcagcaa tctgcagtct    240
gaagacctgg cagattattt ctgccagcaa tatagcctct atcctctcac gttcggtgct    300
gggaccaagg tggagctgaa a                                              321

<210> SEQ ID NO 12
<211> LENGTH: 321
<212> TYPE: DNA
<213> ORGANISM: Artificial sequence
<220> FEATURE:
<221> NAME/KEY: misc_feature
<222> LOCATION: ()..()
<223> OTHER INFORMATION: Synthetic construct of 3B6DIVKv7

<400> SEQUENCE: 12
gacattgtga tgacccagtc tcaaaaatcc atgtccacat cagtaggaga cagggtcagc     60
atctcctgca aggccagtca gaatgtgggt actcctgtag cctggtatca gcagaaacca    120
gaacaatctc ctaaacttct gatttactcg acatccactc ggtaccctgg agtccctgat    180
cgcttcactg gcagtggatc tgggacagat ttcactctca ccatcagcaa tctgcaggct    240
gaagacgtgg cagattattt ctgccagcaa tatagcctct atcctctcac gttcggtgct    300
gggaccaagc tggagctgaa a                                              321
```

CARRIER MOLECULES

CROSS REFERENCE TO RELATED APPLICATIONS

This application claims the benefit of U.S. Provisional Application No. 60/301,154, filed Jun. 26, 2001 and U.S. Provisional Application No. 60/300,947, filed Jun. 27, 2001, the disclosures of which are incorporated herein by reference in their entirety.

FIELD OF THE INVENTION

The present invention relates generally to carrier molecules derived from one animal or avian species or strains and which are substantially non-immunogenic when exposed to an immune system from a species or strain of another animal or avian creature. More particularly, the present invention provides deimmunized immunointeractive molecules and even more particular deimmunized antibodies for use in diagnostic and therapeutic applications.

BACKGROUND OF THE INVENTION

Bibliographic details of the publications referred to in this specification are collected at the end of the description.

Reference to any prior art in this specification is not, and should not be taken as, an acknowledgment or any form of suggestion that this prior art forms part of the common general knowledge in any country.

Fibrinogen is a large protein molecule which normally circulates in blood plasma in a dissolved state. In the presence of thrombin, fibrinogen molecules form long thread-like polymers or networks called fibrin which is the primary ingredient of blood clots.

Upon digestion with plasmin, fibrinogen forms fragments designated A–E. Fragments D and E are the predominant fragments and there is about twice as much D as there is of E. Fibrinogen has a trinodular shape where fragment E is a central component and fragment D is a terminal component.

Plasmin digests of fibrin and fibrinogen can be differentiated from each other using polyacrylamide gel electrophoresis (PAGE). Cross-linking of fibrin with Factor XIIIa forms dimers of fragment D called D-dimer. Factor XIIIa is an enzyme which introduces covalent bonds between adjacent monomers in fibrin (Budzynski et al., *Blood* 54(4): 794–804, 1979). Factor XIIIa is activated by the thrombin-catalyzed removal of a peptide from a precursor in plasma and in blood platelets. D-dimer is a molecule of about 189,000 daltons which consists essentially of two fragment D moieties derived from different fibrin molecules covalently bound by cross-link bonds between the γ chain remnants of fibrinogen. Fibrinogen itself comprises six chains with two copies of an α, β and γ chain.

Another complex (DD)E is formed by plasmin degradation of cross-linked human fibrin and comprises a combination of two D fragments and fragment E.

Other cross-linked derivatives are described by Graeff and Halfer (Graeff and Halfer, "Detection and Relevance of Cross-linked Fibrin Derivatives in Blood", *Seminars in Thrombosis and Hemostatis* 8(1), 1982) and include high molecular weight cross-linked derivatives such as DY, YY, XD, XY, DXD and YXD.

Normal haemostasis or coagulation of blood involves maintaining intravascular constituents in a liquid phase or suspension while concomitantly permitting local deposition of solid phase blood components in areas of vessel damage.

In health, it has been assumed, but never experimentally demonstrated, that a balance exists between a low-grade intravascular deposition of fibrin and its removal by fibrinolysis or cellular phagocytosis.

Early clinical observations revealed that some severely ill patients developed signs of hemorrhage and massive bruising and had prolonged clotting times and thrombocytopenia. At postmorten, in some cases, fibrin thrombin were demonstrated in the microvasculature. The diffuse nature of these thrombin gave rise to disseminated intravascular coagulation (DIC) also known as consumptive coagulopathy. Subsequently, the thrombin were associated with conditions such as deep vein thrombosis (DVT) and pulmonary embolism (PE).

Conditions such as DIC, DVT and PE involve activation of the coagulation system resulting in platelet consumption, thrombin generation, fibrin deposition and secondary fibrinolysis. The net biologic effect of this process reflects a balance between fibrin deposition and fibrin clearance. The resulting clinical manifestations may be haemorrhage, when depletion of coagulation factors predominates, or ischemic tissue damage, due to the effects of vascular occlusion amongst other conditions.

DIC, DVT and PE have been reported as a secondary phenomenon in a wide variety of disorders, particularly those accompanied by a combination of shock, acidosis and hypoxemia. The well-recognized clinical associations are sepsis, major trauma, malignancy and obstetric disorders. Recently, DVT has been recognized as a particular problem during prolonged air travel or other prolonged immobility. In any event, activation of the coagulation sequence results in consumption of coagulation protein and platelets, leading to fibrin deposition in the micro-circulation.

Ideally, a definitive diagnosis of conditions such as DIC, DVT and PE requires the direct demonstration of diffuse fibrin deposition. The practical difficulty of obtaining multiple direct biopsy evidence to differentiate between localized and generalized fibrin formation has led to the development of indirect tests that are substituted as diagnostic end points. However, these tests are not specific for the syndrome of intravascular fibrin deposition. Their specificity is further reduced by the action of other enzymes that although not able to convert fibrinogen to fibrin can cause similar alterations to thrombin on the other coagulation factors involved in thrombosis. All of the indirect tests are based on the principle that thrombin is the only enzyme (snake venoms excluded) capable of converting fibrinogen to fibrin in mammals.

Also, apart from the paracoagulation tests that detect the presence of circulating soluble fibrin monomer complexes, none of the more specific thrombin specific tests is readily available or useful for immediate clinical application in the diagnosis of these fibrin-associated conditions. These tests include the FPA (fibrinopeptide A) test where FPA is measured by a specific RIA procedure, fibrin monomer assays, fibrinogen gel exclusion chromatography and tests for FPB (fibrinopeptide B) or thrombin increasable FPB.

Tests with biochemical non-specificity for thrombin action include the prothrombin time (PT), thromboplastin time (A PTT) and thrombin clotting time (TCT) tests. Although frequently useful in practice, it must be recognized that information obtained from these tests is non-specific in nature, acting as a measure of clotting factor depletion regardless of etiology.

Coagulation factor assays have also been found to be relatively non-specific and these include assays for cofactors V and VIII as well as tests for fibrinogen levels.

Tests for fibrin-fibrinogen degradation products so far have not proved to be specific for the action of plasmin on fibrin and may yield positive results where there has been fibrinogenolysis without prior thrombin action on the fibrinogen molecule. These tests include tests for fragments D and E.

Tests for thrombin-mediated platelet interaction or release have been found to be non-specific in nature. These include platelet count, platelet survival and tests of platelet release.

The use of radio labeled fibrinogen in relation to identifying clotting factors have also been attempted but found to be time consuming and difficult to perform.

Thus, the efficacy of a diagnostic test lies in its ability to indicate the presence or absence of disease. There are well recognized essential design principles for studies determining the efficacy of a diagnostic test which enables the four indices of sensitivity, specificity, positive predictive value and negative predictive value to be determined. The first requirement is the adoption of a suitable standard for diagnosis. Ideally, this standard should be slightly more than a clinical definition and should be as specific as possible for the disease entity. An inherent difficulty in relation to DVT and PE in particular is that many of the routinely available laboratory tests also lack diagnostic specificity. A low platelet count supports the likelihood of these conditions but may occur as an isolated finding secondary to infection. Similar limitations apply to many of the coagulation assays. Hypofibrinogenemia does not distinguish between primary fibrinolysis, due either to the action of plasmin or elastases and secondary fibrinolysis following the thrombin-mediated conversion of fibrinogen to fibrin. Alternatively, sensitive tests of thrombin action are available but there are obvious drawbacks with their clinical use. An example is the FPA assay which, although specific for thrombin action, is exquisitely sensitive and may detect localized intravascular coagulation yielding a positive result in uncomplicated venous thrombosis. The clinical significance of an elevated FPA level, even with a positive paracoagulation test, is then at issue, particularly if the platelet count, global clotting tests and fibrinogen level are normal.

For these reasons, sensitivity, specificity and predictive values cannot be determined in a standard fashion. The clinical presentation of these disorders is complex and unpredictable. The application of the available tests for diagnosis are, therefore, best considered in relation to the different clinical syndromes of intravascular coagulation.

Murine monoclonal antibody 3B6 was disclosed (U.S. Pat. No. 4,758,524). This antibody is specific for D-dimer and represents the first clot-specific antibody. The ability to use this antibody, however, in humans as a systemic diagnostic agent is limited due to the immunogenicity of the molecule. There is a need, therefore, to modify the 3B6 antibody to reduce its immunogenicity in non-murine animals and humans.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

The articles "a" and "an" are used herein to refer to one or to more than one (i.e. to at least one) of the grammatical object of the article. By way of example, "an element" means one element or more than one element.

In work leading up to the present invention, deimmunization technology was used to reduce the immunogenicity of the 3B6 antibody. This has enabled the development of a thrombosis imaging diagnostic procedure for use in humans. Furthermore, the deimmunized form of the 3B6 antibody permits its use as a clot targeting agent to deliver clot dissolution or clot growth prevention agents such as anticoagulants to the site of a clot. The deimmunized molecules of the present invention act, therefore, as carriers of diagnostic and therapeutic agents to a target site such as a clot. The molecules may also have their own diagnostic or therapeutic properties. The development of a deimmunized form of the 3B6 antibody has application for a range of conditions such as DVT and PE. Furthermore, the deimmunized 3B6 antibodies can be used in combination with computer assisted tomographic nuclear medicine or planar imaging techniques such as CT, MRI or ultrasound.

The present invention provides, therefore, a carrier molecule generally in the form of an immunointeractive molecule and in particular a monoclonal antibody rendered chimeric and/or mutated relative to a parent molecule such that it exhibits reduced capacity for immunogenicity in a target host, such as a human. The process of chimerism or mutation is referred to herein as deimmunization. In a particularly preferred embodiment, the immunointeractive molecule such as the monoclonal antibody is humanized to reduce its immunogenicity in humans. Deimmunization may be conducted in different ways but in a preferred embodiment, one or more amino acids in the variable (v) region of a monoclonal antibody are mutated (e.g. substituted) to reduce MHC II recognition of peptides derived from this region. In other words, the deimmunization process is aimed at reducing a T cell epitope-mediated immune response to the antibody. The most preferred antibody of the present invention is a deimmunized form of murine monoclonal antibody 3B6 which exhibits specificity for D-dimer. The generation of a deimmunized form of 3B6 permits development inter alia of a systemic clot targeting agent for blood clots in humans. This permits its use as an imaging agent and as a vehicle to deliver clot dissolution or clot growth prevention agents such as to the site of a clot.

The deimmunized antibody acts, therefore, alone or as a carrier for a range of diagnostic and/or therapeutic agents.

Accordingly, one aspect of the present invention provides a variant of an immunointeractive molecule comprising a portion having specificity for cross-linked fibrin derivatives and which portion is derived from an immunointeractive molecule obtainable from one animal or avian creature wherein the variant exhibits reduced immunogenicity in another animal or avian creature from the same or different species.

Preferably, the immunointeractive molecule is a variant monoclonal antibody comprising a portion having specificity for cross-linked fibrin derivatives.

More preferably, the monoclonal antibody is a variant of a murine-derived monoclonal antibody having specificity for human-derived D-dimer and other cross-linked fibrin derivatives and non-reactivity with fibrinogen or fibrinogen degradation products inclusive of fragments D and E wherein the variant murine-derived monoclonal antibody is substantially non-immunogenic in a human.

Preferably, the antibody is a deimmunized antibody molecule having specificity for an epitope recognized by monoclonal antibody 3B6 and comprises at least one of the complementary determining regions (CDRs) of the variable domain derived from the 3B6 monoclonal antibody and the remaining immunoglobulin-derived parts of the deimmunized antibody molecule are derived from an immunoglobulin or an analogue thereof from the host for which the antibody is to be deimmunized.

The present invention provides, therefore, a deimmunized antibody molecule having specificity for an epitope recognized by monoclonal antibody 3B6 wherein at least one of the complementary determining regions (CDRS) of the variable domain of said deimmunized antibody is derived from the the 3B6 monoclonal antibody wherein one or more amino acids in a variable region of said 3B6 antibody is mutated to reduce MHC class II recognition of peptides derived from this region.

The present invention further provides a variant of murine monoclonal antibody 3B6 deimmunized for use in humans comprising one or more amino acid mutations in the v-region of the 3B6 antibody designed to eliminate or reduce peptide fragments of the v-region associating with MHC class II molecule.

The deimmunized immunointeractive molecules are useful alone or as carriers of diagnostic and/or therapeutic agents to a target site such as a blood clot.

Accordingly, the present invention contemplates a method for detecting a blood clot in a human patient by introducing into the patient a deimmunized form of murine monoclonal antibody 3B6 or an antigen-binding fragment thereof labeled with a reporter molecule allowing dissemination of the labeled antibody throughout the circulatory system and then subjecting the patient to reporter molecule-detection means to identify the location of the antibody in a clot.

In an alternative embodiment, the deimmunized form of 3B6 is not labeled but a second antibody having anti-immunoglobulin specificity is labeled. This antibody forms a labeled complex with the first mentioned antibody.

As a carrier, the deimmunized carrier may deliver any clot binding molecule to the site of a clot as well as other diagnostic or therapeutic agents.

The present invention contemplates, therefore, the use of a deimmunized murine monoclonal antibody specific for D-dimer or other cross-linked fibrin derivatives in the manufacture of clot imaging agent.

Yet another aspect of the present invention contemplates a method for facilitating the dissolution or removal of a blood clot in a human, said method comprising administering to said human a clot dissolution or clot growth prevention-effective amount of a variant murine-derived monoclonal antibody having specificity for human-derived D-dimer and other cross-linked fibrin derivatives and non-reactivity with fibrinogen or fibrinogen degradation products inclusive of fragments D and E wherein said variant murine-derived monoclonal antibody is substantially non-immunogenic in a human wherein said monoclonal antibody further comprises a clot dissolution or clot growth prevention agent fused, bound or otherwise associated thereto.

Still another aspect of the present invention is directed to the use of a variant murine-derived monoclonal antibody having specificity for human-derived D-dimer and other cross-linked fibrin derivatives and non-reactivity with fibrinogen or fibrinogen degradation products inclusive of fragments D and E wherein said variant murine-derived monoclonal antibody is substantially non-immunogenic in a human and said antibody further comprising a clot dissolution or clot growth prevention agent fused, bound or otherwise attached thereto in the manufacture of a medicament for the dissolution of a blot clot in a human.

A preferred molecule is a variant murine monoclonal antibody 3B6 deimmunized for use in humans and comprising a combination of heavy and light chain v-regions comprising the amino acid sequences encoded by nucleotide sequences selected from SEQ ID NO:7/SEQ ID NO:10, SEQ ID NO:8/SEQ ID NO:10, SEQ ID NO:9/SEQ ID NO:10, SEQ ID NO:7/SEQ ID NO:12, SEQ ID NO:8/SEQ ID NO:12, SEQ ID NO:8/SEQ ID NO:11, SEQ ID NO:9/SEQ ID NO:11, SEQ ID NO:9/SEQ ID NO:12 and SEQ ID NO:7/SEQ ID NO:11 or combinations of amino acid sequences encoded by nucleotide sequences having at least 70% similarity to one or both amino acid sequences in each of the above listed pairs or nucleotide sequences capable of hybridizing to low stringency conditions to one or both nucleotide sequences or their complementary forms in each of the above listed pairs.

The variant 3B6 antibody deimmunized for use preferably comprises a combination of heavy and light chain v-regions comprising the amino acid sequences selected from SEQ ID NO:1/SEQ ID NO:4, SEQ ID NO:2/SEQ ID NO:4, SEQ ID NO:3/SEQ ID NO:4, SEQ ID NO:1/SEQ ID NO:6, SEQ ID NO:2/SEQ ID NO:6, SEQ ID NO:2/SEQ ID NO:5, SEQ ID NO:3/SEQ ID NO:5, SEQ ID NO:3/SEQ ID NO:6 and SEQ ID NO:1/SEQ ID NO:5 or combinations of amino acid sequences having at least 70% similarity to one or both amino acid sequences in each of the above listed pairs.

Another preferred variant of 3B6 comprises a combination of heavy and light chain v-regions selected from VHv5/VKv1, VHv6/VKv1, VHv7/VKv1, VHv5/VKv7, VHv6/VKv7, VHv6/VKv4, VHv7/VKv4, VHv7/VKv7 and VHv5/VKv4.

Another aspect of the present invention contemplates a method for detecting a blood clot in a human patient by introducing into the patient a deimmunized form of murine monoclonal antibody 3B6 or an antigen-binding fragment thereof labeled with a reporter molecule allowing dissemination of the labeled antibody throughout the circulatory system and then subjecting the patient to a computer assisted tomographic nuclear medicine scan to visualize the clot.

Yet another aspect of the present invention contemplates a method for detecting a blood clot in a human patient by introducing into the patient a deimmunized form of murine monoclonal antibody 3B6 or an antigen-binding fragment thereof labeled with a reporter molecule allowing dissemination of the labeled antibody throughout the circulatory system and then subjecting said patient to planar clot imaging to visualize the clot.

The deimmunized immunointeractive molecule of the present invention is also useful to anchor an anti-coagulant at a particular site. This aspect provides, therefore, tissue-specific anchoring of a diagnostic or therapeutic agent to, for example, a clot. Furthermore, the immunointeractive molecule may be engineered to have multiple specificities. For example, a bi-specific deimmunized antibody is contemplated which comprises one specificity for a clot and another specificity to a site of a clot (e.g. to a cell receptor). This enables the antibody to remain at the site of the clot.

In an alternative, a multi-step treatment is contemplated where, for example, the deimmunized 3B6 or other interactive molecule conjugated to an anti-coagulant is administered to target the clot and forms a complex and then a second antibody directed to the first antibody and/or the anti-coagulant is administered to enhance or monitor the first complex.

The deimmunized immunointeracative molecule may also be usd to determine the kinetics of clot dissipation or clot disappearance. This is useful to predict even earlier the appearance or disappearance of clots and, hence, aids in determining the kinetics of when to initiate second treatments such as anti-coagulant treatments.

The present invention further provides conjugates comprising the deimmunized immunointeractive molecules and imaging and/or therapeutic tags. Examples of imaging tags include MRI, ultrasound and CT tags. Examples of therapeutic tags include radioactive isotopes, anti-clotting agents and cytokines.

A summary of sequence identifiers used throughout the subject specification is provided in Table 1.

TABLE 1

Summary of Sequence Identifiers

| SEQUENCE ID NO: | DESCRIPTION |
|---|---|
| 1 | Amino acid of 3B6DIVHv5 |
| 2 | Amino acid of 3B6DIVHv6 |
| 3 | Amino acid of 3B6DIVHv7 |
| 4 | Amino acid of 3B6DIVKv1 |
| 5 | Amino acid of 3B6DIVKv4 |
| 6 | Amino acid 3B6DIVKv7 |
| 7 | Nucleotide sequence encoding 3B6DIVHv5 |
| 8 | Nucleotide sequence encoding 3B6DIVHv6 |
| 9 | Nucleotide sequence encoding 3B6DIVHv7 |
| 10 | Nucleotide sequence encoding 3B6DIVKv1 |
| 11 | Nucleotide sequence encoding 3B6DIVKv4 |
| 12 | Nucleotide sequence encoding 3B6DIVKv7 |

BRIEF DESCRIPTION OF THE FIGURES

FIG. 1 is a representation showing (A) a schematic of the 3B6 monoclonal antibody; (B) a photograph of 3B6 binding to blood clots (×4,2000 magnification).

FIG. 2 is a schematic representation of a 3B6 antibody labeled with a nuclear tag ($^{99m}$Tc).

FIG. 3A is a diagrammatic representation showing administration of 3B6 $^{99m}$Tc to the circulatory system of a human.

FIG. 3B is a photographic representation showing visualization of blood clots in the anterior thighs as radiation from $^{99m}$Tc concentrates at the clot site.

FIGS. 4A, 4B and 4C are graphical representations showing D-dimer capture assay using deimmunized 3B6 monoclonal antibodies.

DETAILED DESCRIPTION OF THE PREFERRED EMBODIMENTS

The present invention is predicated in part on the application of biochemical techniques to render an immunointeractive molecule derived from one animal or avian creature substantially non-immunogenic in another animal or avian creature of the same or different species. The biochemical process is referred to herein as "deimmunization". Reference herein to "deimmunization" includes processes such as complementary determinant region (CDR) grafting, "reshaping" with respect to a framework region of an immunointeractive molecule and variable (v) region mutation, all aimed at reducing the immunogenicity of an immunointeractive molecule in a particular host. In the present case, the preferred immunointeractive molecule is an antibody such as a polyclonal or monoclonal antibody. In a most preferred embodiment, the immunointeractive molecule is a monoclonal antibody, derived from one animal or avian creature and which exhibits reduced immunogenicity in another animal or avian creature from the same or different species.

The present invention relates generally to carrier molecules derived from one animal or avian species or strains and which are substantially non-immunogenic when exposed to an immune system from a species or strain of another animal or avian creature. The carrier molecules may exhibit useful diagnostic or therapeutic properties per se or may be used to deliver active compounds (e.g. anti-clotting agents, radioactive isotopes) to a target site. Generally, the carrier molecules are immunointeractive molecules. More particularly, the present invention is directed to a deimmunized including a non-murine mammalianized form of a murine-derived monoclonal antibody substantially incapable of inducing an immune response against itself in a non-murine animal and in particular a human. Even more particularly, the present invention provides a deimmunized form of murine monoclonal antibody 3B6 such that it is incapable of, or exhibits reduced capacity for, inducing a substantial immune response against itself or its derivatives when administered to a human. The deimmunized immunointeractive molecules and in particular antibodies of the present invention have a range of useful diagnostic and therapeutic applications such as in the detection of blood clots in the circulatory system of a human and as a clot targeting agent to deliver a clot dissolution or clot growth prevention agent such as an anticoagulant. The demmunized including humanized forms of the subject monoclonal antibody are particularly useful in the diagnosis and treatment of conditions such as deep vein thrombosis and pulmonary embolism. The molecules of the present invention are particularly useful as agents for delivering active compounds to a target site. Such active compounds include clot binding molecules.

Accordingly, one aspect of the present invention provides a variant of an immunointeractive molecule, said variant comprising a portion having specificity for cross-linked fibrin derivatives and which portion is derived from an immunointeractive molecule obtainable from one animal or avian creature wherein said variant exhibits reduced immunogenicity in another animal or avian creature from the same or different species.

As stated above, the preferred form of immunointeractive molecule is an antibody and in particular a monoclonal antibody.

Accordingly, another aspect of the present invention provides a variant monoclonal antibody comprising a portion having specificity for cross-linked fibrin derivatives and which portion is derived from a monoclonal antibody obtainable from a first animal or avian creature wherein said variant exhibits reduced immunogenicity in a second animal or avian creature from the same or different species.

In a particularly preferred embodiment, a monoclonal antibody is obtained from a murine animal and is deimmunized with respect to another murine animal or a different species of animal such as a human. The murine monoclonal antibody is raised in the murine animal to non-denatured D-dimer which is derived from fibrinogen. The latter molecule is digested by plasmin and generates a range of fragments designated fragments A to E. Cross-linking of fibrin with Factor XIIIa forms dimers of fragment D referred to as "D-dimer". The D-dimer is a molecule of about 189,000 daltons and comprises two fragment D moieties bound by cross-linked bonds between the γ chain remnants of fibrinogen.

Accordingly, another aspect of the present invention is directed to a variant murine-derived monoclonal antibody having specificity for human-derived D-dimer and other cross-linked fibrin derivatives and non-reactivity with fibrinogen or fibrinogen degradation products inclusive of fragments D and E wherein said variant murine-derived monoclonal antibody is substantially non-immunogenic in a human.

Reference to "substantially non-immunogenic" includes reduced immunogenicity compared to a parent antibody, i.e. an antibody before exposure to deimmunization processes. The term "immunogenicity" includes an ability to provoke, induce or otherwise facilitate a humoral and/or T-cell mediated response in a host animal. Particularly convenient immunogenic criteria include the ability for amino acid sequences derived from a variable (v) region of an antibody to interact with MHC class II molecules thereby stimulating or facilitating a T-cell mediating response including a T-cell-assisted humoral response. The immunointeractive molecule and in particular a monoclonal antibody contemplated by the present invention includes reference to a clot targeting agent.

The preferred murine-derived monoclonal antibody is referred to herein as monoclonal antibody 3B6 which is described in U.S. Pat. No. 4,758,524.

Accordingly, in a particularly preferred embodiment, the present invention provides a deimmunized form of monoclonal antibody 3B6 wherein said deimmunized 3B6 is substantially non-immunogenic in humans.

Again, "substantially non-immunogenic" in this context means a reduced capacity of the deimmunized 3B6 monoclonal antibody to induce or facilitate an immune response against itself (following initial or subsequent administration) in a human compared to murine monoclonal antibody 3B6, prior to deimmunization.

Although the preferred invention is particularly directed to a deimmunized form of 3B6 with respect to humans, the present invention extends to this antibody or another antibody with a similar specificity for D-dimer and/or other cross-linked fibrin derivatives deimmunized for any other animal or avian species.

Reference herein to other cross-linked fibrin derivatives includes, for example, in addition to D-dimer, derivatives of D-dimer and a complex comprising D and E fragments. The latter includes (DD)E and is formed by plasmin degradation of cross-linked human fibrin and comprises a combination of two D fragments and fragment E. Other cross-linked derivatives include DY, YY, XD, XY, DXD and YXD where the letters represent fragments of fibrinogen formed following degradation by plasmin wherein X and Y are different and are selected from fragments A to C and E. Preferably, the deimmunized antibody of the subject invention is derived from an antibody specific for D-dimer and other cross-linked fibrin derivatives but which does not cross-react with fibrinogen, fibrinogen degradation products inclusive of fragment D and fragment E. Preferably, the antibody-producing clones are selected using solution phase D-dimer molecules rather than immobilized D-dimer although clones selected by either form of D-dimer are contemplated by the present invention.

Preferably, the deimmunized antibody exhibits an affinity for its target antigen which is similar to the affinity exhibited by murine monoclonal antibody 3B6.

By "affinity" in relation to the interaction between an individual antigen binding site on an antigen-binding molecule and its corresponding site on the antigen includes the strength of this interaction.

By "antibody" is meant a protein of the immunoglobulin family that is capable of combining, interacting or otherwise associating with an antigen. An antibody is, therefore, an antigen-binding molecule. An "antibody" is an example of an immunointeractive molecule and includes a polyclonal or monoclonal antibody. The preferred immunointeractive molecules of the present invention are monoclonal antibodies. An antibody includes parts thereof including Fab portions and antigen-binding determinants.

The term "antigen" is used herein in its broadest sense to refer to a substance that is capable of reacting in and/or inducing an immune response. Reference to an "antigen" includes an antigenic determinant or epitope. The antigen in the present context is regarded as the immunointeractive molecule and, more particularly, a monoclonal antibody.

Any molecule that has binding affinity for a target antigen is referred to as an "antigen-binding molecule". It will be understood that this term extends to immunoglobulins (e.g. polyclonal or monoclonal antibodies), immunoglobulin fragments and non-immunoglobulin derived protein frameworks that exhibit antigen-binding activity. The terms "antibody" and "antigen-binding molecules" include deimmunized forms of these molecules.

That part of an antigenic molecule against which a particular immune response is directed is referred to as an "antigenic determinant" or "epitope" and includes a hapten. Typically, in an animal, antigens present several or even many antigenic determinants simultaneously. A "hapten" is a substance that can combine specificity with an antibody but cannot or only poorly induces an immune response unless bound to a carrier. A hapten typically comprises a single antigenic determinant or epitope.

As stated above, although the preferred antibodies of the present invention are deimmunized forms of murine monoclonal antibodies for use in humans, the subject invention extends to antibodies from any source and deimmunized for use in any host. Examples of animal and avian sources and hosts include humans, primates, livestock animals (e.g. sheep, cows, horses, pigs, donkeys), laboratory test animals (e.g. mice, rabbits, guinea pigs, hamsters), companion animals (e.g. dogs, cats), poultry bird (e.g. chickens, ducks, geese, turkeys) and game birds (e.g. pheasants). The deimmunized antibodies or part thereof may also be generated in non-animal tissues such as plants. Plants are particularly useful as a source of single chain antibodies.

Another aspect of the present invention contemplates a method for generating a deimmunized monoclonal antibody having specificity for antigenic determinants on human D-dimer or other cross-linked fibrin derivatives, said method comprising:

(i) obtaining a cross-linked fibrin derivative or extract containing same from a human;

(ii) generating an antibody in a non-human animal specific to said cross-linked fibrin derivative but which does not cross-react with fragment D; and (iii) subjecting said non-human derived antibody to deimmunization means.

The cross-linked fibrin derivative may be derived from any suitable antigenic extract including plasmin-mediated degradation of fibrin clots or by simultaneous action of thrombin, Factor XIIIa and plasmin on fibrinogen with transient clot formation and subsequent clot lysis. In the latter method, the fibrinogen is converted to fibrin by the action of thrombin and Factor XIIIa and subsequently digested with plasmin. It will, of course, be appreciated that the fibrin derivative or extract containing same may be obtained from an animal source other than human. The antigenic source is conveniently from a biological sample.

A sample that may be extracted, untreated, treated, diluted or concentrated from an animal is included in the term "biological sample".

The above method of obtaining the crude antigenic fraction represents an in vitro method. A suitable in vivo method includes obtaining sera or other body fluid containing the cross-linked fibrin derivative from an animal including human and subjecting the body fluid to a PAGE process wherein substantially pure cross-linked fibrin derivative is isolated.

Alternatively, cross-linked fibrin derivatives may be purified from serum obtained from patients suffering severe thrombotic disorders based on a technique using gel filtration in combination with ion exchange chromatography as described by Willner et al., *Biochemistry* 21: 2687–2692, 1982.

The antigen (i.e. D-dimer or other cross-linked fibrin derivative) can be separated from the biological sample by any suitable means. For example, the separation may take advantage of any one or more of the antigen's surface charge properties, size, density, biological activity and its affinity for another entity (e.g. another protein or chemical compound to which it binds or otherwise associates). Thus, for example, separation of the antigen from the biological fluid may be achieved by any one or more of ultra-centrifugation, ion-exchange chromatography (e.g. anion exchange chromatography, cation exchange chromatography), electrophoresis (e.g. polyacrylamide gel electrophoresis, isoelectric focussing), size separation (e.g., gel filtration, ultra-filtration) and affinity-mediated separation (e.g. immunoaffinity separation including, but not limited to, magnetic bead separation such as Dynabead™ separation, immunochromatography, immuno-precipitation). Choice of the separation technique(s) employed may depend on the biological activity or physical properties of the particular antigen.

Preferably, the separation of the antigen from the biological fluid preserves conformational epitopes present on the antigen surface and, thus, suitably avoids techniques that cause denaturation of the antigen. Persons of skill in the art will recognize the importance of maintaining or mimicking as close as possible physiological conditions peculiar to the antigen (e.g. the biological fluid from which they are obtained) to ensure that the antigenic determinants or active site/s on the antigen, which are exposed to the animal, are structurally identical to that of the native antigen. This ensures the raising of appropriate antibodies in the immunised animal that would recognize the native antigen. In a preferred embodiment of this type, the antigen is separated from the biological fluid using any one or more of affinity separation, gel filtration and ultra-filtration.

Immunization and subsequent production of monoclonal antibodies can be carried out using standard protocols as for example described by Köhler and Milstein (*Nature* 256: 495–499, 1975; Köhler and Milstein, *Eur. J. Immunol.* 6(7): 511–519, 1976), Coligan et al. (*Current Protocols in Immunology*, John Wiley & Sons, Inc., 1991–1997) or Toyama et al. ("*Monoclonal Antibody, Experiment Manual*", published by Kodansha Scientific, 1987). Essentially, an animal is immunized with an antigen-containing biological fluid or fraction thereof by standard methods to produce antibody-producing cells, particularly antibody-producing somatic cells (e.g. B lymphocytes). These cells can then be removed from the immunized animal for immortalization. The antigen may need to first be associated with a larger molecule. The latter is any substance of typically high molecular weight to which a non- or poorly immunogenic substance (e.g. a hapten) is naturally or artificially linked to enhance its immunogenicity.

Immortalization of antibody-producing cells may be carried out using methods, which are well-known in the art. For example, the immortalization may be achieved by the transformation method using Epstein-Barr virus (EBV) (Kozbor et al., *Methods in Enzymology* 121: 140, 1986). In a preferred embodiment, antibody-producing cells are immortalized using the cell fusion method (described in Coligan et al., 1991–1997, supra), which is widely employed for the production of monoclonal antibodies. In this method, somatic antibody-producing cells with the potential to produce antibodies, particularly B cells, are fused with a myeloma cell line. These somatic cells may be derived from the lymph nodes, spleens and peripheral blood of primed animals, preferably rodent animals such as mice and rats. In the exemplary embodiment of this invention mice, spleen cells are used. It would be possible, however, to use rat, rabbit, sheep or goat cells, or cells from other animal species instead.

Specialized myeloma cell lines have been developed from lymphocytic tumours for use in hybridoma-producing fusion procedures (Köhler and Milstein, 1976, supra; Shulman et al., *Nature* 276: 269–270, 1978; Volk et al., *J. Virol.* 42(1): 220–227, 1982). These cell lines have been developed for at least three reasons. The first is to facilitate the selection of fused hybridomas from unfused and similarly indefinitely self-propagating myeloma cells. Usually, this is accomplished by using myelomas with enzyme deficiencies that render them incapable of growing in certain selective media that support the growth of hybridomas. The second reason arises from the inherent ability of lymphocytic tumour cells to produce their own antibodies. To eliminate the production of tumour cell antibodies by the hybridomas, myeloma cell lines incapable of producing endogenous light or heavy immunoglobulin chains are used. A third reason for selection of these cell lines is for their suitability and efficiency for fusion.

Many myeloma cell lines may be used for the production of fused cell hybrids, including, e.g. P3X63-Ag8, P3X63-AG8.653, P3/NS1-Ag4–1 (NS-1), Sp2/0-Ag14 and S194/5.XXO.Bu.1. The P3X63-Ag8 and NS-1 cell lines have been described by Köhler and Milstein (1976, supra). Shulman et al. (1978, supra) developed the Sp2/0-Ag14 myeloma line. The S194/5.XXO.Bu.1 line was reported by Trowbridge (*J. Exp. Med.* 148(1): 313–323, 1978).

Methods for generating hybrids of antibody-producing spleen or lymph node cells and myeloma cells usually involve mixing somatic cells with myeloma cells in a 10:1 proportion (although the proportion may vary from about 20:1 to about 1:1), respectively, in the presence of an agent or agents (chemical, viral or electrical) that promotes the fusion of cell membranes. Fusion methods have been described (Köhler and Milstein, 1975, supra; Köhler and Milstein, 1976, supra; Gefter et al., *Somatic Cell Genet.* 3: 231–236, 1977; Volk et al., 1982, supra). The fusion-promoting agents used by those investigators were Sendai virus and polyethylene glycol (PEG).

Because fusion procedures produce viable hybrids at very low frequency (e.g. when spleens are used as a source of somatic cells, only one hybrid is obtained for roughly every $1 \times 10^5$ spleen cells), it is preferable to have a means of selecting the fused cell hybrids from the remaining unfused cells, particularly the unfused myeloma cells. A means of detecting the desired antibody-producing hybridomas among other resulting fused cell hybrids is also necessary. Generally, the selection of fused cell hybrids is accomplished by culturing the cells in media that support the growth of hybridomas but prevent the growth of the unfused myeloma cells, which normally would go on dividing indefinitely. The somatic cells used in the fusion do not maintain long-term viability in in vitro culture and hence do not pose a problem. In the example of the present invention, myeloma cells lacking hypoxanthine phosphoribosyl transferase (HPRT-negative) were used. Selection against these cells is made in hypoxanthine/aminopterin/thymidine (HAT) medium, a medium in which the fused cell hybrids survive due to the HPRT-positive genotype of the spleen cells. The use of myeloma cells with different genetic deficiencies (drug sensitivities, etc.) that can be selected against in media supporting the growth of genotypically competent hybrids is also possible.

Several weeks are required to selectively culture the fused cell hybrids. Early in this time period, it is necessary to identify those hybrids which produce the desired antibody, so that they may subsequently be cloned and propagated. Generally, around 10% of the hybrids obtained produce the desired antibody, although a range of from about 1 to about 30% is not uncommon. The detection of antibody-producing hybrids can be achieved by any one of several standard assay methods, including enzyme-linked immunoassay and radioimmunoassay techniques as, for example, described in Kennet et al. ((eds) *Monoclonal Antibodies and Hybridomas: A New Dimension in Biological Analyses*, pp. 376–384, Plenum Press, New York, 1980). In a particularly preferred embodiment, an enyme linked immunosorbent assay (ELISA) is performed to selected antibody producing clones using solution phase D-dimer.

Once the desired fused cell hybrids have been selected and cloned into individual antibody-producing cell lines, each cell line may be propagated in either of two standard ways. A suspension of the hybridoma cells can be injected into a histocompatible animal. The injected animal will then develop tumours that secrete the specific monoclonal antibody produced by the fused cell hybrid. The body fluids of the animal, such as serum or ascites fluid, can be tapped to provide monoclonal antibodies in high concentration. Alternatively, the individual cell lines may be propagated in vitro in laboratory culture vessels. The culture medium containing high concentrations of a single specific monoclonal antibody can be harvested by decantation, filtration or centrifugation, and subsequently purified.

The cell lines are tested for their specificity to detect the antigen of interest by any suitable immunodetection means. For example, cell lines can be aliquoted into a number of wells and incubated and the supernatant from each well is analyzed by enzyme-linked immunosorbent assay (ELISA), indirect fluorescent antibody technique, or the like. The cell line(s) producing a monoclonal antibody capable of recognizing the target antigen but which does not recognize non-target epitopes are identified and then directly cultured in vitro or injected into a histocompatible animal to form tumours and to produce, collect and purify the required antibodies.

Thus, the present invention provides in a first step monoclonal antibodies which specifically interact with D-dimer or other cross-linked fibrin derivative.

As indicated above, non-animal cells such as a plant, yeast and/or microbial cells may be used to generate typically single-chain antibodies. In this embodiment, such cells are engineered to express nucleic acid molecules which encode a chain of an antibody.

The monoclonal antibody is then subjected to deimmunization means. Such a process may take any of a number of forms including the preparation of chimeric antibodies which have the same or similar specificity as the monoclonal antibodies prepared according to the present invention. Chimeric antibodies are antibodies whose light and heavy chain genes have been constructed, typically by genetic engineering, from immunoglobulin variable and constant region genes belonging to different species. Thus, in accordance with the present invention, once a hybridoma producing the desired monoclonal antibody is obtained, techniques are used to produce interspecific monoclonal antibodies wherein the binding region of one species is combined with a non-binding region of the antibody of another species (Liu et al., *Proc. Natl. Acad. Sci. USA* 84: 3439–3443, 1987). For example, the CDRs from a non-human (e.g. murine) monoclonal antibody can be grafted onto a human antibody, thereby "humanizing" the murine antibody (European Patent Publication No. 0 239 400; Jones et al., *Nature* 321: 522–525, 1986; Verhoeyen et al., *Science* 239: 1534–1536, 1988; Riechmann et al., *Nature* 332: 323–327, 1988). In this case, the deimmunizing process is specific for humans. More particularly, the CDRs can be grafted onto a human antibody variable region with or without human constant regions. The non-human antibody providing the CDRs is typically referred to as the "donor" and the human antibody providing the framework is typically referred to as the "acceptor". Constant regions need not be present, but if they are, they must be substantially identical to human immunoglobulin constant regions, i.e. at least about 85–90%, preferably about 95% or more identical. Hence, all parts of a humanized antibody, except possibly the CDRs, are substantially identical to corresponding parts of natural human immunoglobulin sequences. Thus, a "humanized antibody" is an antibody comprising a humanized light chain and a humanized heavy chain immunoglobulin. A donor antibody is said to be "humanized", by the process of "humanization", because the resultant humanized antibody is expected to bind to the same antigen as the donor antibody that provides the CDRs. Reference herein to "humanized" includes reference to an antibody deimmunized to a particular host, in this case, a human host.

It will be understood that the deimmunized antibodies may have additional conservative amino acid substitutions which have substantially no effect on antigen binding or other immunoglobulin functions. Exemplary conservative substitutions may be made according to Table 2.

TABLE 2

| ORIGINAL RESIDUE | EXEMPLARY SUBSTITUTIONS |
|---|---|
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Exemplary methods which may be employed to produce deimmunized antibodies according to the present invention are described, for example, in Richmann et al., 1988, supra; U.S. Pat. Nos. 6,056,957, 6,180,370 and 6,180,377 and Chothia et al., *J. Mol. Biol.* 196: 901, 1987.

Thus, in one embodiment, the present invention contemplates a deimmunized antibody molecule having specificity for an epitope recognized by monoclonal antibody 3B6 wherein at least one or at least two or at least three or at least four or at least five of the complementary determining regions (CDRs) of the variable domain of said deimmunized antibody is derived from said 3B6 monoclonal antibody and the remaining immunoglobulin-derived parts of the deimmunized antibody molecule are derived from an immunoglobulin or an analogue thereof from the host for which the antibody is to be deimmunized.

This aspect of the present invention involves manipulation of the framework region of a non-human antibody.

Preferably, the deimmunized antibody is a humanized form of murine 3B6.

One preferred deimmunization process is referred to herein a variable(v)-region grafting and results in a chimeric antibody. The resulting antibody comprises one or more amino acid substitutions within the v-region when compared to the present (e.g. murine) antibody. The rationale for making v-region changes is to further the potential for an induced immune response in the intended host (e.g. a human). The basis of deimmunization is predicated in part on the assumption that a substantive immune response to an introduced antibody requires a T-cell mediated response. The trigger for the T-cell response is the presentation of processed peptides emanating from the introduced antibody on the surface of antigen presenting cells (APCs). The APCs present such peptides in association with surface MHC class II molecules. The deimmunized approach is, therefore, based on:

(i) predicting peptide sequences capable of associating with MHC class II molecules; and (ii) changing strategic residues to eliminate the ability of the peptide to associate with the MHC class II molecule.

Accordingly, another aspect of the present invention provides a variant of murine monoclonal antibody 3B6 deimmunized for use in humans, said variant comprising one or more amino acid mutations in the v-region of said 3B6 antibody to eliminate or reduce peptide fragments of said v-region associating with MHC class II molecules.

One or more amino acid substitutions, additions and/or deletions or one or more nucleotide substitutions, additions and/or deletions is encompassed by the term "mutation" or "mutations".

In a particularly preferred embodiment, the deimmunized antibodies are generated by co-transfection of different combinations of three deimmunized H-chain genes and three deimmunized L-chain genes. The resulting variants are derived from different combinations encoded by H-chain and L-chain genes. Preferred H-chains are Hv5, Hv6 and Hv7. These are referred to herein as 3B6DIVHv5 (SEQ ID NO:1), 3B6DIVHv6 (SEQ ID NO:2) and 3B6DIVHv7 (SEQ ID NO:3). Preferred L-chains are Kv1, Kv4 and Kv7. These are referred to herein as 3B6DIVKv1 (SEQ ID NO:4), 3B6DIVKv4 (SEQ ID NO:5) and 3B6DIVKv7 (SEQ ID NO:6). Particularly useful combinations include VHv5/VKv1, VHv6/VKv1, VHv7/VKv1, VHv5/VKv7, VHv6/VKv7, VHv6/VKv4, VHv7/VKv4, VHv7/VKv7 and VHv5/VKv4. The sequence identifer numbers (SEQ ID NOS:) in parentheses represent the amino acid sequences of the particular chains. Corresponding nucleotide sequences encoding each of SEQ ID NOS: 1–6 are represented by SEQ ID NOS: 7–12.

All such combinations of H and L chains are also encompassed by the present invention.

Accordingly, the present invention provides a variant murine monoclonal antibody 3B6 deimmunized for use in humans, said variant comprising a combination of heavy and light chain v-regions comprising the amino acid sequences encoded by nucleotide sequences selected from SEQ ID NO:7/SEQ ID NO:10, SEQ ID NO:8/SEQ ID NO:10, SEQ ID NO:9/SEQ ID NO:10, SEQ ID NO:7/SEQ ID NO:12, SEQ ID NO:8/SEQ ID NO:12, SEQ ID NO:8/SEQ ID NO:11, SEQ ID NO:9/SEQ ID NO:11, SEQ ID NO:9/SEQ ID NO:12 and SEQ ID NO:7/SEQ ID NO:11 or combinations of amino acid sequences encoded by nucleotide sequences having at least 70% similarity to one or both amino acid sequences in each of the above listed pairs or nucleotide sequences capable of hybridizing to low stringency conditions to one or both nucleotide sequences or their complementary forms in each of the above listed pairs.

All such combinations of H and L chains are also encompassed by the present invention.

Accordingly, the present invention provides a variant murine monoclonal antibody 3B6 deimmunized for use in humans, said variant comprising a combination of heavy and light chain v-regions comprising the amino acid sequences selected from SEQ ID NO:1/SEQ ID NO:4, SEQ ID NO:2/SEQ ID NO:4, SEQ ID NO:3/SEQ ID NO:4, SEQ ID NO:1/SEQ ID NO:6, SEQ ID NO:2/SEQ ID NO:6, SEQ ID NO:2/SEQ ID NO:5, SEQ ID NO:3/SEQ ID NO:5, SEQ ID NO:3/SEQ ID NO:6 and SEQ ID NO:1/SEQ ID NO:5 or combinations of amino acid sequences encoded by nucleotide sequences having at least 70% similarity to one or both amino acid sequences in each of the above listed pairs.

More particularly, the present invention provides a variant of a murine monoclonal antibody 3B6 deimmunized for use in humans, said variant comprising a combination of heavy and light chain v-regions selected from VHv5/VKv1, VHv6/VKv1, VHv7/VKv1, VHv5/VKv7, VHv6/VKv7, VHv6/VKv4, VHv7/VKv4, VHv7/VKv7 and VHv5/VKv4.

The term "similarity" as used herein includes exact identity between compared sequences at the nucleotide or amino acid level. Where there is non-identity at the nucleotide level, "similarity" includes differences between sequences which result in different amino acids that are nevertheless related to each other at the structural, functional, biochemical and/or conformational levels. Where there is non-identity at the amino acid level, "similarity" includes amino acids that are nevertheless related to each other at the structural, functional, biochemical and/or conformational levels. In a particularly preferred embodiment, nucleotide and sequence comparisons are made at the level of identity rather than similarity.

Terms used to describe sequence relationships between two or more polynucleotides or polypeptides include "reference sequence", "comparison window", "sequence similarity", "sequence identity", "percentage of sequence similarity", "percentage of sequence identity", "substantially similar" and "substantial identity". A "reference sequence" is at least 12 but frequently 15 to 18 and often at least 25 or above, such as 30 monomer units, inclusive of nucleotides and amino acid residues, in length. Because two polynucleotides may each comprise (1) a sequence (i.e. only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of typically 12 contiguous residues that is compared to a reference sequence. The comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerised implementations of algorithms (GAP, BESTFIT, FASTA, and TFASTA in the Wisconsin Genetics Software Package Release 7.0, Genetics Computer Group, 575 Science Drive Madison, Wis, USA) or by inspection and the best alignment (i.e. resulting in the highest percentage homology over the comparison window) generated by any of the various methods selected. Reference also may be made to the BLAST family of programs as, for example, disclosed by Altschul et al. (*Nucl. Acids Res.* 25: 3389–3402. 1997). A detailed discussion of sequence analysis can be found in Unit 19.3 of Ausubel et al. ("Current Protocols in Molecular Biology" John Wiley & Sons Inc, 1994–1998, Chapter 15).

The terms "sequence similarity" and "sequence identity" as used herein refers to the extent that sequences are identical or functionally or structurally similar on a nucleotide-by-nucleotide basis or an amino acid-by-amino acid basis over a window of comparison. Thus, a "percentage of sequence identity", for example, is calculated by comparing two optimally aligned sequences over the window of comparison, determining the number of positions at which the identical nucleic acid base (e.g. A, T, C, G, I) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. For the purposes of the present invention, "sequence identity" will be understood to mean the "match percentage" calculated by the DNASIS computer program (Version 2.5 for windows; available from Hitachi Software engineering Co., Ltd., South San Francisco, Calif., USA) using standard defaults as used in the reference manual accompanying the software. Similar comments apply in relation to sequence similarity.

Mutations and derivatives contemplated by the present invention include redundant mutations in nucleotide sequences which do not result in a change in amino acid sequence.

Reference herein to a low stringency includes and encompasses from at least about 0 to at least about 15% v/v formamide and from at least about 1 M to at least about 2 M salt for hybridization, and at least about 1 M to at least about 2 M salt for washing conditions. Generally, low stringency is at from about 25–30° C. to about 42° C. The temperature may be altered and higher temperatures used to replace formamide and/or to give alternative stringency conditions. Alternative stringency conditions may be applied where necessary, such as medium stringency, which includes and encompasses from at least about 16% v/v to at least about 30% v/v formamide and from at least about 0.5 M to at least about 0.9 M salt for hybridization, and at least about 0.5 M to at least about 0.9 M salt for washing conditions, or high stringency, which includes and encompasses from at least about 31% v/v to at least about 50% v/v formamide and from at least about 0.01 M to at least about 0.15 M salt for hybridization, and at least about 0.01 M to at least about 0.15 M salt for washing conditions. In general, washing is carried out $T_m=69.3+0.41$ (G+C)% (Marmur and Doty, *J. Mol. Biol.* 5: 109, 1962). However, the $T_m$ of a duplex DNA decreases by 1° C. with every increase of 1% in the number of mismatch base pairs (Bonner and Laskey, *J. Mol. Biol.* 5: 109, 1962). Formamide is optional in these hybridization conditions. Accordingly, particularly preferred levels of stringency are defined as follows: low stringency is 6×SSC buffer, 0.1% w/v SDS at 25–42° C.; a moderate stringency is 2×SSC buffer, 0.1% w/v SDS at a temperature in the range 20° C. to 65° C.; high stringency is 0.1×SSC buffer, 0.1% w/v SDS at a temperature of at least 65° C.

As used herein, the term "CDR" includes CDR structural loops which covers to the three light chain and the three heavy chain regions in the variable portion of an antibody framework region which bridge β strands on the binding portion of the molecule. These loops have characteristic canonical structures (Chothia et al., *J. Mol. Biol.* 227: 799, 1992; Kabat et al., "*Sequences of Proteins of Immunological Interest*", U.S. Department of Health and Human Services, 1983).

An immunoglobulin light or heavy chain variable region, which is interrupted by three hypervariable regions, also called CDRs, is referred to herein as a "framework region". The extent of the framework region and CDRs have been precisely defined (see, for example, Krebber et al., *J. Immunol. Methods* 201(1): 35–55, 19). The sequences of the framework regions of different light or heavy chains are relatively conserved within a species. As used herein, a "human framework region" is a framework region that is substantially identical (about 85% or more, usually 90–95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

As used herein, the term "heavy chain variable region" means a polypeptide which is from about 110 to 125 amino acid residues in length, the amino acid sequence of which corresponds to that of a heavy chain of a monoclonal antibody of the invention, starting from the amino-terminal (N-terminal) amino acid residue of the heavy chain. Likewise, the term "light chain variable region" means a polypeptide which is from about 95 to 130 amino acid residues in length, the amino acid sequence of which corresponds to that of a light chain of a monoclonal antibody of the invention, starting from the N-terminal amino acid residue of the light chain. Full-length immunoglobulin "light chains" (about 25 Kd or 214 amino acids) are encoded by a variable region gene at the $NH_2$-terminus (about 110 amino acids) and a κ or λ constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g. γ (encoding about 330 amino acids).

The term "immunogenicity" is used herein in its broadest sense to include the property of evoking an immune response within an organism. Immunogenicity typically depends partly upon the size of the substance in question, and partly upon how unlike host molecules it is. It is generally considered that highly conserved proteins tend to have rather low immunogenicity.

The term "immunoglobulin" is used herein to refer to a protein consisting of one or more polypeptides substantially encoded by immunoglobulin genes. The recognized immunoglobulin genes include the κ, λ, α, γ ($IgG_1$, $IgG_2$, $IgG_3$, $IgG_4$), δ, ε and μ constant region genes, as well as the myriad immunoglobulin variable region genes. One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, Fab' and (Fab')$_2$.

Reference herein to "immuno-interactive" includes reference to any interaction, reaction, or other form of association between molecules and in particular where one of the molecules is, or mimics, a component of the immune system. An "immunointeractive molecule" includes an antibody, antibody fragment, synthetic antibody or a T-cell associated binding molecule (TABM).

By "isolated" is meant material that is substantially or essentially free from components that normally accompany it in its native state.

A sample of biological fluid that is isolated from, or derived from, a particular source of the host is described as being "obtained from".

The invention also contemplates the use and generation of fragments of monoclonal antibodies produced by the method of the present invention including, for example, Fv, Fab, Fab' and F(ab')$_2$ fragments. Such fragments may be prepared by standard methods as for example described by Coligan et al. (1991–1997, supra).

The present invention also contemplates synthetic or recombinant antigen-binding molecules with the same or similar specificity as the monoclonal antibodies of the invention. Antigen binding molecules of this type may comprise a synthetic stabilized Fv fragment. Exemplary fragments of this type include single chain Fv fragments (sFv, frequently termed scFv) in which a peptide linker is used to bridge the N terminus or C terminus of a $V_H$ domain with the C terminus or N-terminus, respectively, of a $V_L$ domain. ScFv lack all constant parts of whole antibodies and are not able to activate complement. Suitable peptide linkers for joining the $V_H$ and $V_L$ domains are those which allow the $V_H$ and $V_L$ domains to fold into a single polypeptide chain having an antigen binding site with a three dimensional structure similar to that of the antigen binding site of a whole antibody from which the Fv fragment is derived. Linkers having the desired properties may be obtained by the method disclosed in U.S. Pat. No 4,946,778. However, in some cases a linker is absent. ScFvs may be prepared, for example, in accordance with methods outlined in Krebber et al. (1997, supra). Alternatively, they may be prepared by methods described in U.S. Pat. No 5,091,513, European Patent No 239,400 or the articles by Winter and Milstein (*Nature* 349: 293, 1991) and Plückthun et al. (In *Antibody engineering: A practical approach* 203–252, 1996).

Alternatively, the synthetic stabilised Fv fragment comprises a disulphide stabilized Fv (dsFv) in which cysteine residues are introduced into the $V_H$ and $V_L$ domains such that in the fully folded Fv molecule the two residues will form a disulphide bond therebetween. Suitable methods of producing dsFv are described, for example, in (Glockshuber et al., *Biochem.* 29: 1363–1367, 1990; Reiter et al., *J. Biol. Chem.* 269: 18327–18331, 1994; Reiter et al., *Biochem.* 33: 5451–5459, 1994; Reiter et al., *Cancer Res.* 54: 2714–2718, 1994; Webber et al., *Mol. Immunol.* 32: 249–258, 1995).

Also contemplated as synthetic or recombinant antigen-binding molecules are single variable region domains (termed dAbs), as, for example, disclosed in (Ward et al., *Nature* 341: 544–546, 1989; Hamers-Casterman et al., *Nature* 363: 446–448, 1993; Davies & Riechmann, *FEBS Lett.* 339: 285–290, 1994).

Alternatively, the synthetic or recombinant antigen-binding molecule may comprise a "minibody". In this regard, minibodies are small versions of whole antibodies, which encode in a single chain the essential elements of a whole antibody. Suitably, the minibody is comprised of the $V_H$ and $V_L$ domains of a native antibody fused to the hinge region and CH3 domain of the immunoglobulin molecule as, for example, disclosed in U.S. Pat. No 5,837,821.

In an alternate embodiment, the synthetic or recombinant antigen binding molecule may comprise non-immunoglobulin derived, protein frameworks. For example, reference may be made to Ku & Schutz (*Proc. Natl. Acad. Sci. USA* 92: 6552–6556, 1995) which discloses a four-helix bundle protein cytochrome b562 having two loops randomized to create complementarity determining regions (CDRs), which have been selected for antigen binding.

The synthetic or recombinant antigen-binding molecule may be multivalent (i.e. having more than one antigen binding site). Such multivalent molecules may be specific for one or more antigens. Multivalent molecules of this type may be prepared by dimerization of two antibody fragments through a cysteinyl-containing peptide as, for example disclosed by (Adams et al., *Cancer Res.* 53: 4026–4034, 1993; Cumber et al., *J. Immunol.* 149: 120–126, 1992;). Alternatively, dimerization may be facilitated by fusion of the antibody fragments to amphiphilic helices that naturally dimerize (Plünckthun, *Biochem.* 31: 1579–1584, 1992) or by use of domains (such as leucine zippers jun and fos) that preferentially heterodimerize (Kostelny et al., *J. Immunol.* 148: 1547–1553, 1992). In further embodiment, a multi-step process is employed such as first administering a deimmunized antibody and then an anti-antibody with, for example, a reporter molecule.

The present invention further encompasses chemical analogues of amino acids in the variant antibodies. The use of chemical analogues of amino acids is useful inter alia to stabilize the molecules when administered to a subject. The analogues of the amino acids contemplated herein include, but are not limited to, modifications of side chains, incorporation of unnatural amino acids and/or their derivatives during peptide, polypeptide or protein synthesis and the use of crosslinkers and other methods which impose conformational constraints on the proteinaceous molecule or their analogues.

Examples of side chain modifications contemplated by the present invention include modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivitisation, for example, to a corresponding amide.

Sulphydryl groups may be modified by methods such as carboxymethylation with iodoacetic acid or iodoacetamide; performic acid oxidation to cysteic acid; formation of a mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carbethoxylation with diethylpyrocarbonate.

Examples of incorporating unnatural amino acids and derivatives during peptide synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acid, contemplated herein is shown in Table 3.

TABLE 3

| Non-conventional amino acid | Code | Non-conventional amino acid | Code |
| --- | --- | --- | --- |
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| | | L-N-methylaspartic acid | Nmasp |
| aminoisobutyric acid | Aib | L-N-methylcysteine | Nmcys |
| aminonorbornyl-carboxylate | Norb | L-N-methylglutamine | Nmgln |
| | | L-N-methylglutamic acid | Nmglu |
| cyclohexylalanine | Chexa | L-Nmethylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucine | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | α-methyl-aminoisobutyrate | Maib |
| D-valine | Dval | α-methyl-γ-aminobutyrate | Mgabu |
| D-α-methylalanine | Dmala | α-methylcyclohexylalanine | Mehexa |
| D-α-methylarginine | Dmarg | α-methylcylcopentylalanine | Mepen |
| D-α-methylasparagine | Dmasn | α-methyl-α-napthylalanine | Manap |
| D-α-methylaspartate | Dmasp | α-methylpenicillamine | Mpen |
| D-α-methylcysteine | Dmcys | N-(4-aminobutyl)glycine | Nglu |
| D-α-methylglutamine | Dmgln | N-(2-aminoethyl)glycine | Naeg |
| D-α-methylhistidine | Dmhis | N-(3-aminopropyl)glycine | Norn |
| D-α-methylisoleucine | Dmile | N-amino-α-methylbutyrate | Nmaabu |
| D-α-methylleucine | Dmleu | α-napthylalanine | Anap |
| D-α-methyllysine | Dmlys | N-benzylglycine | Nphe |
| D-α-methylmethionine | Dmmet | N-(2-carbamylethyl)glycine | Ngln |

TABLE 3-continued

| Non-conventional amino acid | Code | Non-conventional amino acid | Code |
| --- | --- | --- | --- |
| D-α-methylornithine | Dmorn | N-(carbamylmethyl)glycine | Nasn |
| D-α-methylphenylalanine | Dmphe | N-(2-carboxyethyl)glycine | Nglu |
| D-α-methylproline | Dmpro | N-(carboxymethyl)glycine | Nasp |
| D-α-methylserine | Dmser | N-cyclobutylglycine | Ncbut |
| D-α-methylthreonine | Dmthr | N-cycloheptylglycine | Nchep |
| D-α-methyltryptophan | Dmtrp | N-cyclohexylglycine | Nchex |
| D-α-methyltyrosine | Dmty | N-cyclodecylglycine | Ncdec |
| D-α-methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(-1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl-γ-aminobutyrate | Nmgabu |
| N-methyl-cyclohexylalanine | Nmchexa | D-N-methylmethionine | Dnmmet |
| D-N-methylornithine | Dnmom | N-methylcyclopentylalanine | Nmcpen |
| N-methylglycine | Nala | D-N-methylphenylalanine | Dnmphe |
| N-methyl-aminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methyltbreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| γ-aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenyl-alanine | Hphe | L-α-methylalanine | Mala |
| L-α-methylarginine | Marg | L-α-methylasparagine | Masn |
| L-α-methylaspartate | Masp | L-α-methyl-t-butylglycine | Mtbug |
| L-α-methylcysteine | Mcys | L-methylethylglycine | Metg |
| L-α-methylglutamine | Mgln | L-α-methylglutamate | Mglu |
| L-α-methylhistidine | Mhis | L-α-methyl-homophenylalanine | Mhphe |
| L-α-methylisoleucine | Mile | N-(2-methylthioethyl)glycine | Nmet |
| L-α-methylleucine | Mleu | L-α-methyllysine | Mlys |
| L-α-methylmethionine | Mmet | L-α-methylnorleucine | Mnle |
| L-α-methylnorvaline | Mnva | L-α-methylornithine | Mom |
| L-α-methylphenylalanine | Mphe | L-α-methylproline | Mpro |
| L-α-methylserine | Mser | L-α-methylthreonine | Mthr |
| L-α-methyltryptophan | Mtrp | L-α-methyltyrosine | Mtyr |
| L-α-methylvaline | Mval | L-N-methyl-homophenylalanine | Nmhphe |
| N-(N-(2,2-diphenylethyl)carbamylmethyl) | Nnbhm | N-(N-(3,3-diphenylpropyl)carbamylmethyl)glycine | Nnbhe |

TABLE 3-continued

| Non-conventional amino acid | Code | Non-conventional amino acid | Code |
|---|---|---|---|
| glycine 1-carboxy-1-(2,2-diphenyl-ethylamino)-cyclopropane | Nmbc | | |

Crosslinkers can be used, for example, to stabilize 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety such as maleimido or dithio moiety (SH) or carbodiimide (COOH). In addition, peptides can be conformationally constrained by, for example, incorporation of $C_\alpha$ and N $_\alpha$-methylamino acids, introduction of double bonds between $C_\alpha$ and $C_\beta$ atoms of amino acids and the formation of cyclic peptides or analogues by introducing covalent bonds such as forming an amide bond between the N and C termini, between two side chains or between a side chain and the N or C terminus.

A monoclonal antibody obtained before deimmunization may be identified by any number of means including the steps of:

(a) coating a surface with antigen selected from cross-linked fibrin derivative or extract containing same or fibrinogen degradation product;

(b) contacting the antigen in step (a) with monoclonal antibody derived from fibrin cross-linked derivative prepared as described above; and (c) subjecting the complex formed in step (b) to a signal amplification step.

Suitably, in step (a), a well plate may be utilized in which cross-linked fibrin derivatives such as D-dimer and/or fibrinogen degradation product (preferably obtained from a procedure wherein fibrinogen was suitably digested with thrombin to obtain fragment D, fragment E and optionally fragments X and Y) was applied to the individual wells.

Subsequently, monoclonal antibody derived from a cross-linked fibrin derivative was then added to each well. An appropriate signal amplification step which may be applied is an EIA step wherein an appropriate enzyme conjugate may be coupled to the complex and substrate subsequently added. Alternatively, RIA, FIA, agglutination, adherence or chemiluminescence may be used as appropriate signal amplification steps.

The purpose of the screening assay procedure referred to above is to ensure that the cells being tested are producing antibody specific to the relevant cross-linked fibrin derivative, but not to fragment D.

There should be minimal reaction with fibrinogen or fibrinogen degradation products and a positive reaction with the derivative. The term "minimal" includes no reactivity but extends to basal levels such as compared to an antibody-directed to fibrinogen per se. Consequently, a minimal reaction includes sub-optimal reactivity compared to a fibrinogen-specific antibody.

The present invention also includes within its scope an assay to detect linked fibrin derivatives including the steps of:

(1) contacting a monoclonal antibody specific to cross-linked fibrin derivatives but not fragment D with a biological sample suspected of containing an antigen derived from a cross-linked fibrin derivative or comprising a cross-linked fibrin derivative per se; and (2) subjecting the complex formed in step (1) to a signal amplification step.

In the above-mentioned assay, the cross-linked fibrin derivative is suitably D-dimer, $D_2E$ or any other derivative of a high molecular weight nature as described above. The monoclonal antibody is prepared as described previously which is relevant to the particular cross-linked fibrin derivative being assayed.

The presence of the cross-linked fibrin derivative may be used as a suitable diagnostic aid for prethrombotic, thrombotic or other conditions that involve the formation and lysis of fibrin.

The deimmunized monoclonal antibody of the present invention is particularly useful for blood clot imaging as well as for targeting blood clots in order to bring the clot into contact with enzymes or other chemical agents capable of dissolving, wholly or partially, the clot.

With respect to clot imaging, a reporter molecule is attached to the deimmunized monoclonal antibody or to an antibody having specificity for the deimmunized antibody or a portion or conjugate thereon and this is then introduced to a host, such as a human. By detecting the reporter molecule, blood clots can be visualized. One particularly useful form of reporter molecule is a nuclear tag. Nuclear tags contemplated for use in the present invention include but not limited to a bifunctional metal ion chelate. The chelate may be attached to the antibody itself or multiple chelates may be attached to the protein via dendrimers. Particularly preferred nuclear tags are $^{99m}Tc$, $^{18}F$, $^{64}Cu$, $^{67}Ga$, $^{68}Ga$, $^{77}Br$, $^{97}Ru$, $^{111}In$, $^{123}I$, $^{124}I$, $^{131}I$ and $^{188}Re$. The most preferred nuclear tag is $^{99m}Tc$. Preferably, the host is a human and, hence, it is necessary for the 3B6 murine monoclonal antibody to be deimmunized.

Alternative forms of immunoscintigraphy may be obtained using isotopes such as a $^{68}Ga$ or $^{124}I$ or other PET isotopes. Such technology may be described as "immuno-PET". The technology has advantages over γ camera scintigraphy and may provide high resolution images of blood clots especially in areas of the body less amenable to conventional diagnostic means such as lungs or small clots in the calf or pelvis.

Accordingly, the present invention provides a conjugate molecule comprising a deimmunized immunointeractive molecule such as a deimmunized antibody and one or both of an imaging tag or a therapeutic agent.

Preferred imaging tags are MRI-, ultrasound- and/or CT-type tags such as but not limited to $^{99m}Tc$, $^{18}F$, $^{64}Cu$, $^{67}Ga$, $^{68}Ga$, $^{77}Br$, $^{97}Ru$, 111In, $^{123}I$, $^{124}I$, $^{131}I$ and $^{188}Re$.

Preferred therapeutic tags include cytokines, anti-clotting agents, wound-repairing agents and anti-infection agents.

Another aspect of the present invention contemplates a method for detecting a blood clot in a human patient, said method comprising introducing into said patient a deimmunized form of murine monoclonal antibody 3B6 or an antigen-binding fragment thereof labeled with a reporter molecule allowing dissemination of the labeled antibody throughout the circulatory system and then subjecting said patient to reporter molecule-detection means to identify the location of the antibody in a clot.

Preferably, the reporter molecule is a nuclear tag.

Preferably, the nuclear tag is $^{99m}Tc$, $^{18}F$, $^{64}Cu$, $^{67}Ga$, $^{68}Ga$, $^{77}Br$, $^{97}Ru$, $^{111}In$, $^{123}I$, $^{124}I$, $^{131}I$ and $^{188}Re$.

Preferably, the nuclear tag is $^{99m}$Tc.

The present invention further contemplates the use of a deimmunized murine monoclonal antibody specific for D-dimer or other cross-linked fibrin derivatives in the manufacture of clot imaging agent.

Preferably, the murine monoclonal antibody is 3B6 or a homologue thereof.

Preferably, the clot imaging tag is for use in humans.

The same antibody may also carry multiple tages such as multiple anti-coagulant agents and/or reporter molecules. Alternatively, or in addition, multiple anti-antibodies may be administered each carrying a different tag.

The present clot targeting antibody may be used alone or in combination with other imaging protocols. One such protocol is planar imaging such as but not limited to CT, MRI or ultrasound.

Accordingly, another aspect of the present invention contemplates a method for detecting a blood clot in a human patient, said method comprising introducing into said patient a deimmunized form of murine monoclonal antibody 3B6 or an antigen-binding fragment thereof labeled with a reporter molecule allowing dissemination of the labeled antibody throughout the circulatory system and then subjecting said patient to planar clot imaging.

Preferably, the planar imaging is MRI or CT scanning. Ultrasound may also be used in the imaging process.

Accordingly, another aspect of the present invention contemplates a method for detecting a blood clot in a human patient, said method comprising introducing into said patient a deimmunized form of murine monoclonal antibody 3B6 or an antigen-binding fragment thereof labeled with a reporter molecule allowing dissemination of the labeled antibody throughout the circulatory system and then subjecting said patient to a computer assisted tomographic nuclear medicine scan to visualize the clot.

Preferably, the reporter molecule is a nuclear tag.

Preferably, the nuclear tag is $^{99m}$Tc, $^{18}$F, $^{64}$Cu, $^{67}$Ga, $^{68}$Ga, $^{77}$Br, $^{97}$Ru, $^{111}$In, $^{123}$I, $^{124}$I, 131I and $^{188}$Re.

Preferably, the nuclear tag is $^{99m}$Tc.

The clot imaging agents of the present invention are also useful as therapeutic agents. In particular, the clot targeting agents are fused, bound or otherwise associated with a clot dissolution or clot growth prevention agent such as an anticoagulant molecule.

Accordingly, another aspect of the present invention contemplates a method for facilitating the dissolution or removal of a blood clot in a human, said method comprising administering to said human a clot dissolution or clot growth prevention-effective amount of a variant murine-derived monoclonal antibody having specificity for human-derived D-dimer and other cross-linked fibrin derivatives and non-reactivity with fibrinogen or fibrinogen degradation products inclusive of fragments D and E wherein said variant murine-derived monoclonal antibody is substantially non-immunogenic in a human wherein said monoclonal antibody further comprises a clot dissolution or clot growth prevention agent fused, bound or otherwise associated thereto.

Yet another aspect of the present invention is directed to the use of a variant murine-derived monoclonal antibody having specificity for human-derived D-dimer and other cross-linked fibrin derivatives and non-reactivity with fibrinogen or fibrinogen degradation products inclusive of fragments D and E wherein said variant murine-derived monoclonal antibody is substantially non-immunogenic in a human and said antibody further comprising a clot dissolution or clot growth prevention agent fused, bound or otherwise attached thereto in the manufacture of a medicament for the dissolution of a blot clot in a human.

In an alternative embodiment, multiple deimmunized antibodies may be used. In one example, a deimmunized 3B6 antibody is administered alone and then deimmunized anti-immunglobulin antibodies each carrying an agent such as a diagnostic or therapeutic agent which will target a clot-3B6 complex. Yet another alternative is to engineer antibodies with multiple (e.g. bi-) specificities. In this case, one specificity may be to the clot and another to the site of the clot (e.g. to a cell receptor). This may also be accomplished using multiple antibodies.

The present invention further contemplates compositions comprising the clot targeting agents of the present invention and one or more pharmaceutically acceptable carriers and/or diluents.

The pharmaceutical forms suitable for injectable use include sterile aqueous solutions as well as as lyophilized forms of antibody preparations together with stabilizing agents such as sugar, proteins or other compounds or molecules which facilitate the radiolabeling process. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization.

Pharmaceutically acceptable carriers and/or diluents include any and all solvents, dispersion media, coatings, anti-bacterial and anti-fungal agents, isotonic and absorption delaying agents and the like. The use of such media and agents for pharmaceutical active substances is well known in the art and except insofar as any conventional media or agent is incompatible with the active ingredient, their use in the therapeutic compositions is contemplated. Supplementary active ingredients can also be incorporated into the compositions.

The clot targeting agents of the present invention are useful for the diagnosis and/or treatment of thrombin-associated conditions such as DVT, PE and DIC.

Yet another aspect of the present invention contemplates a method for treating a subject with cancer associated with fibrin. In this embodiment, antibodies to the D-dimer epitope may be used to deliver cytotoxic agents such as an isotope that emits β or γ emission or combinations threof. Such isotopes include but are not limited to $^{131}$I, yttrium-90, rhenium-186, rhenium-188, lutetium-117 and copper-67. Fibrin associated with a cancer includes a fibrin encapsulated tumor.

The deimmunized immunointeractive molecules of the present invention are, therefore, carriers for any clot binding agents or clot dissolving agents or for any agents which have useful diagnostic or therapeutic properties. The deimmunized immunointeractive molecules of the present invention are also useful for determining the kinetics of clot dissolution, dissipation and/or disappearance. One this information is available, clot dissolving or imaging agents can very quickly be administered.

The present invention is further described by the following non-limiting Examples.

EXAMPLE 1

Cell Fusion and Selection of Hybrids

Spleens were removed aseptically from 2 immunized mice killed by cervical dislocation three days after an injection of D-dimer. Previously, the mice had been immunized with three injections of fibrin lysate digested with proteolytic enzymes thrombin and plasmin as reported in the aforementioned Graeff and Hafter reference. Two spleens were placed in a 60 mm Petri dish (Falcon, 3001, Oxnard, Calif.) containing 5 ml complete medium (85% RPMI 1640, 15% w/v fetal calf serum, 100 I.U./ml penicillin, 100 µg/ml streptomycin and $2 \times 10^{-3}$ M glutamine; Gibco, Grand Island, N.Y.). A cell suspension was prepared by decapsulating the spleen with 2×18 gauge needles attached to 3 ml disposable syringes with the last cm of the tip bent through an angle of 60°. The cell suspension was then aspirated into a 10 ml syringe fitted with a 22 gauge needle and ejected with moderate pressure. This operation was performed twice before filtering the cells into a Falcon 2001 tube through a fine mesh stainless steel screen to remove larger cell clumps and debris.

The cell suspension was allowed to stand for 5 minutes at room temperature to allow smaller clumps and membrane fragments to settle before transferring the cell suspension to a fresh Falcon 2001 tube. The cells were centrifuged at 350 G for 5 minutes at room temperature and the supernatant was decanted from the first cell pellet to a fresh tube and spun at 700 G for five minutes to give a second cell pellet and the two pellets were pooled and resuspended in 5 ml complete medium. The spleen white blood cells (SWBC) were then counted and their viability estimated by Turks and Trypan blue stains, respectively, and $100 \times 10^6$ viable SWBC were placed in separate Falcon 2001 tubes in a total volume of 5 ml complete medium. The NS-1 myeloma cells to be used for fusion, were washed once by centrifugation at 380 G for 15 minutes at room temperature and adjusted to $5 \times 10^6$ viable cells/ml in complete medium.

Twenty-five$\times 10^6$ NS-1 and $100 \times 10^5$ immune SWBC were mixed and spun at 350 G for 5 minutes at room temperature. The supernatant was decanted, the remaining medium was carefully removed with a Pasteur pipette and 2 ml of a 42% w/v solution of polyethylene glycol (PEG, MW1540) (Baker Chemical Co., New Jersey). In RPMI 1640 containing 15% v/v dimethyl sulfoxide (DMSO) at 37° C. was added with a 5 ml glass disposable pipette (Corning Glass, Corning, N.Y.) and the cells were resuspended with the same 5 ml pipette for 30 seconds with the aid of an electric pipetter (Pipet-aid Drummond Scientific Co., Broomall, Pa.). The PEG-cell suspension was allowed to stand for a further 30 seconds at room temperature before adding 5 ml complete medium, dropwise, with a Pasteur pipette, over a period of 90 seconds with constant flicking of the tube, sufficient to ensure complete mixing with the viscous PEG solution. A further 5 ml complete medium was immediately added and mixed by inversion and the cell suspension was allowed to stand for a further 150 seconds at room temperature before centrifugation at 350 G for 5 minutes at room temperature. The supernatant was decanted and the cell pellet was gently resuspended in 5 ml complete medium using a 5 ml pipette with the electric pipetter; extreme care was taken not to break up all cell clumps. Using a Tridak stepper (Bellco Glass Inc., Vineland, N.J.), 0.05 ml of the cell suspension was added to each well of 4 Costar 24 well plates (Costar 3524, Cambridge, Mass.) containing $1 \times 10^6$ normal BALB/c mouse SWBC as feeder cells in 1 ml complete medium containing $10^{-4}$ M Hypoxanthine (Sigma), $4 \times 10^{-7}$ M Aminopterin (Sigma), $1.6 \times 10^{-5}$ M Thymidine (Sigma) and $4 \times 10^{-5}$ M 2-Mercaptoethanol (HAT medium), hereinafter referred to as 1° fusion plates.

The 1° fusion plates were then placed in a humidified 5% $CO_2$ 95% air atmosphere at 37° C. The cells were first fed either on days 5 or 7 and thereafter when necessary, with 0.5 ml fresh HAT medium. Generally, on day 10, 0.5 ml of the medium was removed for the screening assay from each well showing hybridoma growth and 0.5 ml fresh HAT medium was replaced. A number of the strongest growth wells were chosen for maintenance on the basis of the screening assay. The chosen wells were allowed to grow to confluency in the original original well (1° well), then each was split in half and transferred to a fresh well (2° well) of a 24 well Costar plate (2° plate). The wells were checked daily and expanded to a second, third or fourth well of the 2° Costar plate when necessary. From days 14–28, cells were fed with HT medium. When there was strong growth in at least two wells of the 2° plate, supernatant from one well of each clonotype was chosen for rescreening and a number of specific antibody producing clonotypes were chosen from the results of the second screening assay to produce monoclonal antibody secreting cell lines by limiting dilution.

EXAMPLE 2

Cloning of Hybridomas

One 2° well of each chosen clonotype was resuspended and the number of viable cells per well was estimated by Trypan blue exclusion. Immediately before plating each clonotype, the relevant series of dilutions were made in HT medium or complete medium (if the cells were older than 28 days post fusion) to give a frequency of 0.5 cells/0.05 ml. This volume was then added with a Tridak stepper to each well of a 96 well flat bottomed tissue culture plate (Flow Laboratories, Mississauga, Ontario, Canada) (LD plate) containing $1 \times 10^5$ normal mouse spleen feeder cells in 0.1 ml HT or complete medium. the LD plates were then placed in a 37° C. humidified 5% $CO^2$, 95% air atmosphere and screened for clonal growth 7–10 days later. From each positive growth well, 0.1 ml supernatant was removed for screening and these wells were fed for the first time with 0.1–0.15 ml HT or complete medium. On the basis of the LD screening assay, a minimum of two of the "better" specific antibody-producing clones were finally selected for expansion to mass culture.

Alternatively, if it was desired to obtain a large amount of Mab, female BALB/c mice were given an intraperitoneal injection of 0, 5 ml 2, 5, 10, 14, tetramethylpentadecane (Pristane, Aldrich Chemical Corp., Milwaukee, Wis.) 14 days prior to the injection of $2 \times 10^6$ viable hybridoma cells and ascites fluids were collected from the mice 12–14 days after injection of the cells. The ascitic fluid was clarified by centrifugation and MAb recovered by precipitation with 45% ammonium sulphate and stored at either 4° C. or −70° C. in phosphate buffered saline (PBS) containing 0.01% sodium azide.

EXAMPLE 3

Monoclonal Antibody Screening Assay

The wells of a 96 well U bottomed microtest plate (Disposable Products Pty. Ltd., Adelaide, South Australia) were coated by adding 50 µl of either D-dimer (5 µg/ml) or Fibrinogen degradation products (5 µg/ml in PBS for one hour at room temperature (25° C.). Excess antigen was removed by inverting and tapping the plate and the plate was then washed three times with PBS containing 0.05% w/v Tween 20 (Sigma Chemical Corp., St Louis, Mo.). Clones secreting MAb to D-dimer or Fibrinogen degradation products were then detected by adding 50 µl of tissue culture supernatant to each well and incubating for one hour at room temperature. Unbound MAb was removed by inversion and tapping and the plate was washed three times with PBS/Tween. One hundred µl of a 1/1000 dilution of peroxidase conjugated rabbit anti-mouse immunoglobulin (Dakopatts, Copenhagen, Denmark) in PBS/Tween was added and allowed to incubate a further one hour at room temperature. The plate was again inverted and washed three times with PBS/Tween and 100 µl of activated substrate (immediately before use, 10 µl of 3% solution of hydrogen peroxide was added to 10 ml of a substrate solution containing 50 mM citrate, 2.5 mM of 0-tolidine dihydrochloride (0-tolidine, Sigma Chemical Co., recrystallized from dilute HCl) 0.025 mM EDTA pH 4.5) was added to each well. The colour reaction was stopped after 10 minutes by the addition of 50 µl of 3M HCl which caused a colour change from blue to yellow and the absorbance was recorded at 450 nm on a Titertek multiskan.

EXAMPLE 4

Identification of 3B6 Variable Region Sequences

The murine hybridoma 3B6 was propagated in RPMI 1640 medium supplemented with 15% w/v fetal calf serum. Total RNA was prepared from $10^7$ hybridoma cells. $V_H$ and $V^K$ cDNA was prepared using reverse transcriptase and mouse κ constant region and mouse κ constant region primers. The first strand cDNAs were amplified by PCR using a variety of mouse signal sequence primers (6 sets for $V_H$ and 7 sets for $V_K$). The amplified DNAs were gel-purified and cloned into the vector pGem® T Easy (Promega). The $V_H$ and $V_K$ clones obtained were screened for inserts of the expected size by PCR and the DNA sequence of selected clones determined by the dideoxy chain termination method.

Productive $V_H$ and $V_K$ genes were identified by sequence analysis. The location of the complementarity determining regions (CDRs) was determined with reference to other antibody sequences (43). The 3B6 $V_H$ can be assigned to mouse heavy chains sub-group IA. The 3B6 $V_K$ can be assigned to mouse κ chains sub-group I.

EXAMPLE 5

Analysis of 3B6 Variable (v) Region Sequences with Potential T Cell Epitopes

3B6 $V_H$ and $V_K$ sequences were analyzed for the presence of potential T cell epitopes using procedures described previously (Carr et al., International Patent Publication No. WO 98/52976). The peptides identified as potential T cell epitopes (MHC class II binding peptides) were modified in silico and the modified sequence re-analyzed to ensure loss of potential MHC class II binding and verify that further MHC class II binding motifs had not been generated in the surrounding sequence. Alternatively, the sequence was modified to convert the MHC class II binding motif to one found in the human germ line. Single, generally conservative, amino acid substitutions were tested and substitutions made with due regard to overall antibody structure. A number of variant sequences are compiled for the $V_H$ and $V_K$, each containing different numbers of substitutions.

EXAMPLE 6

Designer Variant 3B6 Variable (v) Regions Sequences with Reduced Numbers of Potential T Cell Epitopes The heavy and light (v) regions designed according the scheme of Example 5 were constructed in vitro by the method of overlapping PCR recombination described (Daugherty et al., *Nucleic Acids Research* 19: 2471–2476, 1991). The cloned murine $V_H$ and $V_K$ genes were used as templates for mutagenesis of the framework regions to the required humanized sequences. Sets of mutagenic primer pairs were synthesized encompassing the regions to be altered. Adjacent primers included 15 bp of homologous sequence. A first round of PCR using these primers produced 5 to 8 overlapping DNA fragments encompassing the designed (v) region gene. The vectors $V_H$-PCR1 and $V_K$-PCR1 (Orlandi et al., *Proc. Natl. Acad. Sci. USA* 86: 3833–3837, 1989) were used as templates to introduce 5' flanking sequence including the leader signal peptide, leader intron and the murine immunoglobulin promoter, and 3' flanking sequence including the splice site and intron sequences, in an additional two overlapping fragments. The DNA fragments produced were combined in a second round of PCR using outer flanking primers to obtain PCR products of the required full length. These PCR products were cloned into the vector pUC19 for DNA sequence determination. Clones were selected that contained the expected sequence alterations and the entire DNA sequence was confirmed to be correct for each desired $V_H$ and $V_K$. The heavy and light chain genes were transferred to the expression vectors pSVgpt and pSVhyg with human IgG1 or κ constant regions as described (Tempest et al., *Biotechnology* 9: 266–271, 1991). The vectors $V_H$-PCR1 and $V_K$-PCR1 (Orlandi et al., 1989, supra) were used as templates to introduce 5' flanking sequence including the leader signal peptide, leader intron and the murine immunoglobulin promoter, and 3' flanking sequence including the splice site and intron sequences.

EXAMPLE 7

Expression and Purification of Variant 3B6 Antibodies

The variant 3B6 heavy and light chain expression vectors were co-transfected in different combinations by electroporation into NS0, a non-immunoglobulin producing mouse myeloma, obtained from the European Collection of Animal Cell Cultures, Porton, U.K. (ECACC No 85110505). Colonies expressing the gpt gene were selected in Dulbecco's Modified Eagle's Medium (DMEM) supplemented with 0.8 µg/ml mycophenolic acid and 250 µg/ml xanthine. Production of human antibody by transfected cell clones was measured by ELISA for human IgG (48). Cell lines secreting antibody were selected and expanded. Variant 3B6 antibodies were purified using Prosep®-A (Bioprocessing Ltd, Conset, U.K.).

EXAMPLE 8

Functional Testing of Variant 3B6 Antibodies

Figure 4A:
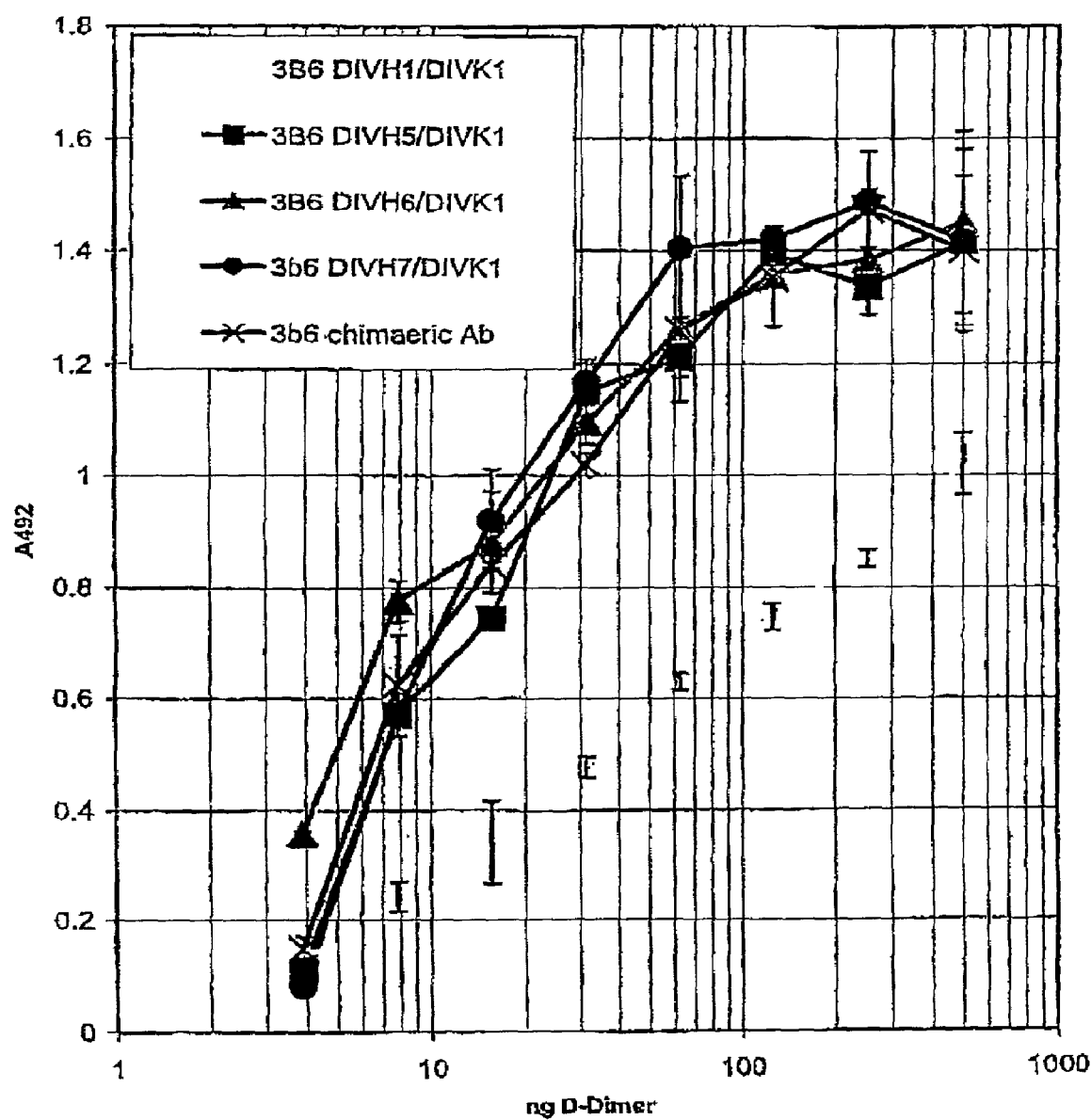
Figure 4B:
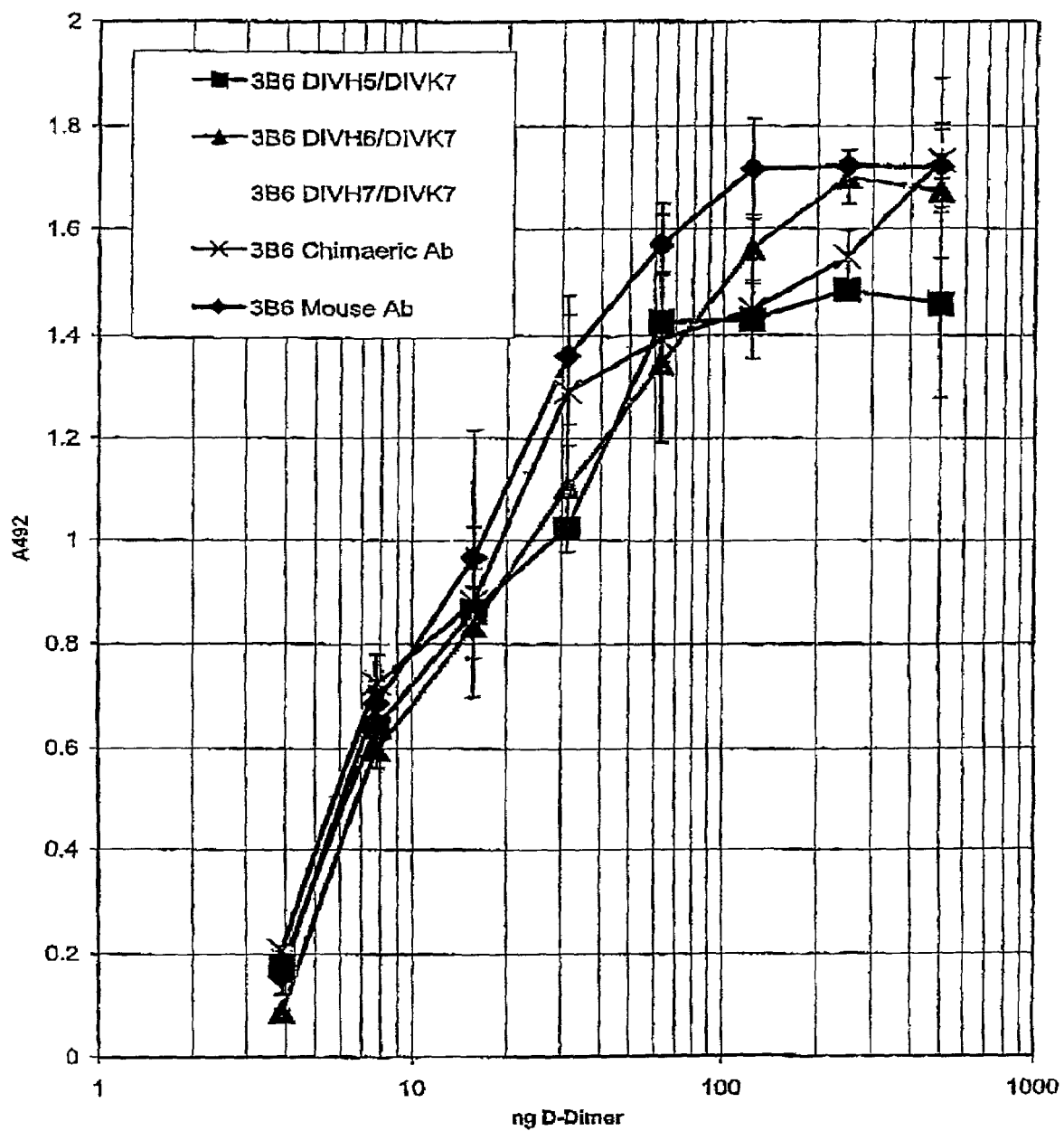
Figure 4C:
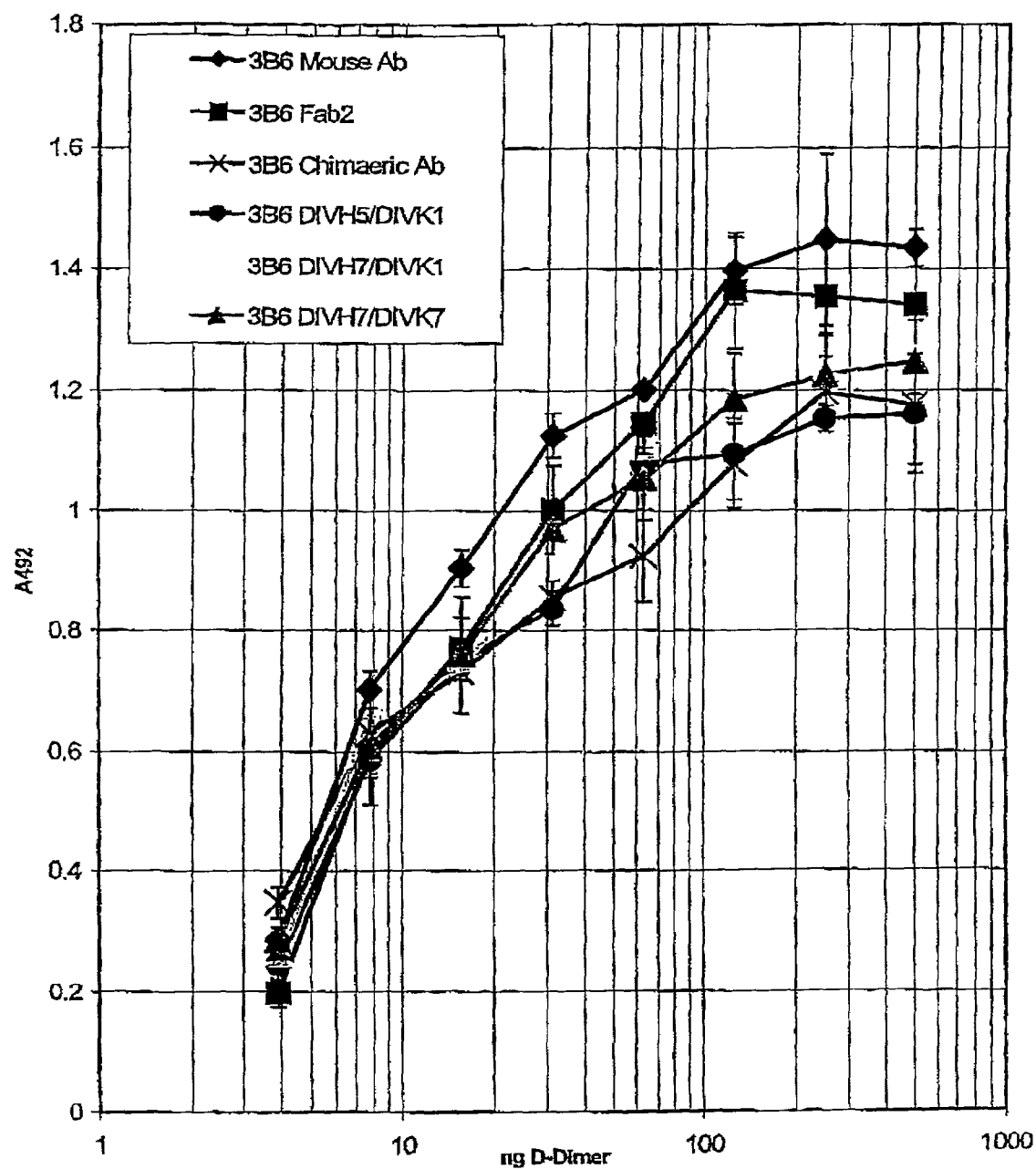

Variant antibodies were tested for D-dimer binding using ELISA based assays broadly as described in Example 3. Binding specificity was confirmed using the human fibrinogen binding assay. In a preferred embodiment, however, the D-dimer was used in solution phase. In this assay, the 3B6 antibodies were coated on the ELISA plate at 0.5 µg/well, to capture D-dimer in solution. D-dimer was applied at 10 µg/ml (500 ng/well) and doubling dilutions. The revealing antibody was HRPO conjugated mouse monoclonal anti-D (Dimertest EIA Tag; Agen) and the results were developed by OPD substrate and read a 492 nm. The deimmunized 3B6 antibodies are compared to the murine and chimeric 3B6 antibodies and the previous lead deimmunized antibody 3B6 DIVH1/DIVK1. The results are shown in FIGS. 4A, 4B and 4C. The use of solution phase D-dimer proved better than solid phase D-dimer in the selection of clones and is a preferred aspect of the present invention.

EXAMPLE 9

Thromboviewing using 3B6-99mTc

Figure 1B:
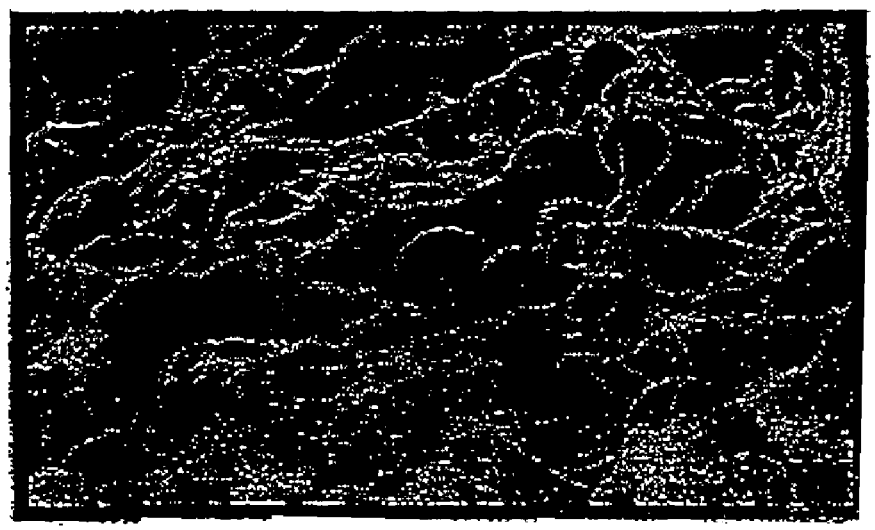
Figure 2:
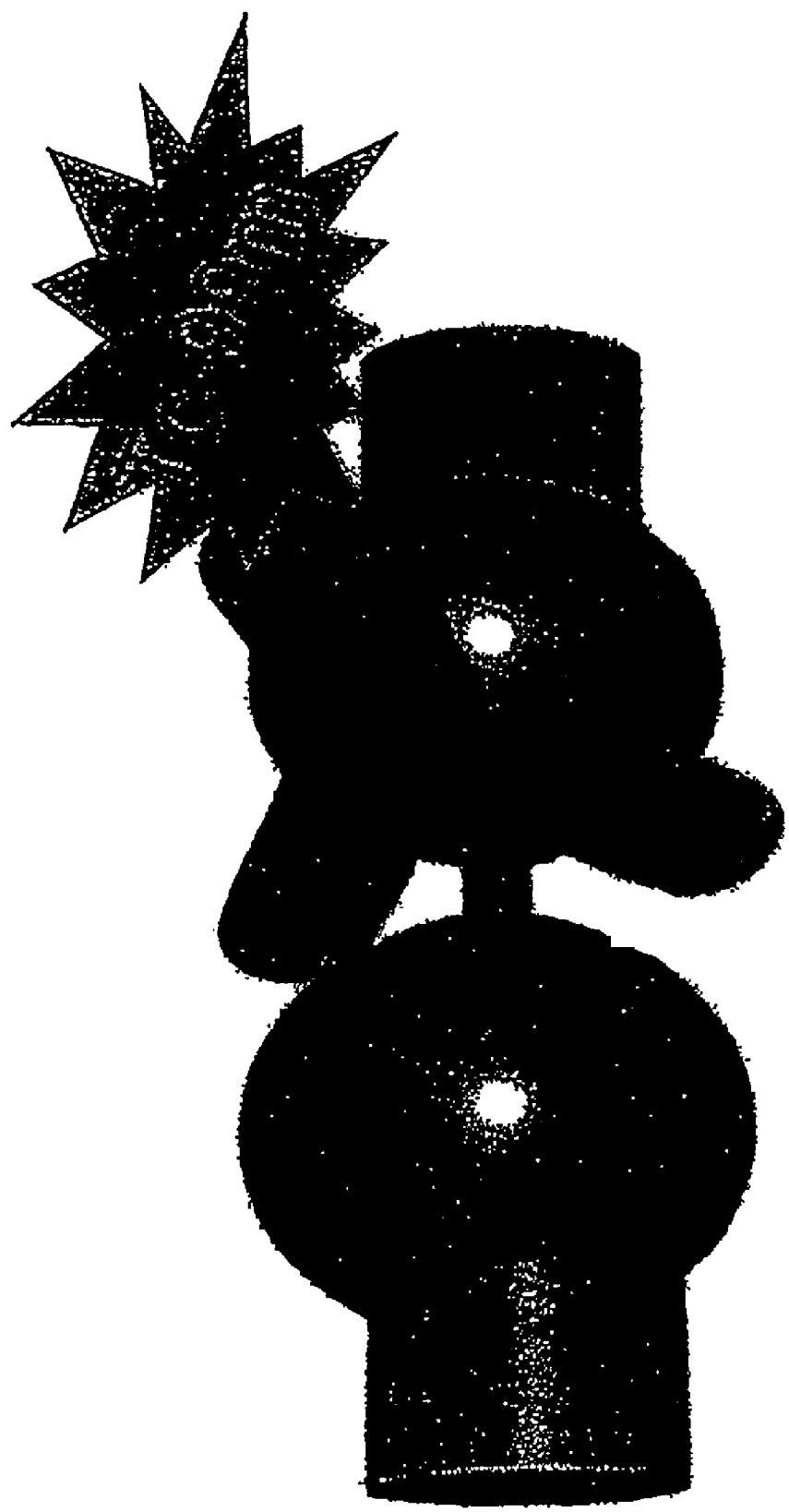
Figure 3A:
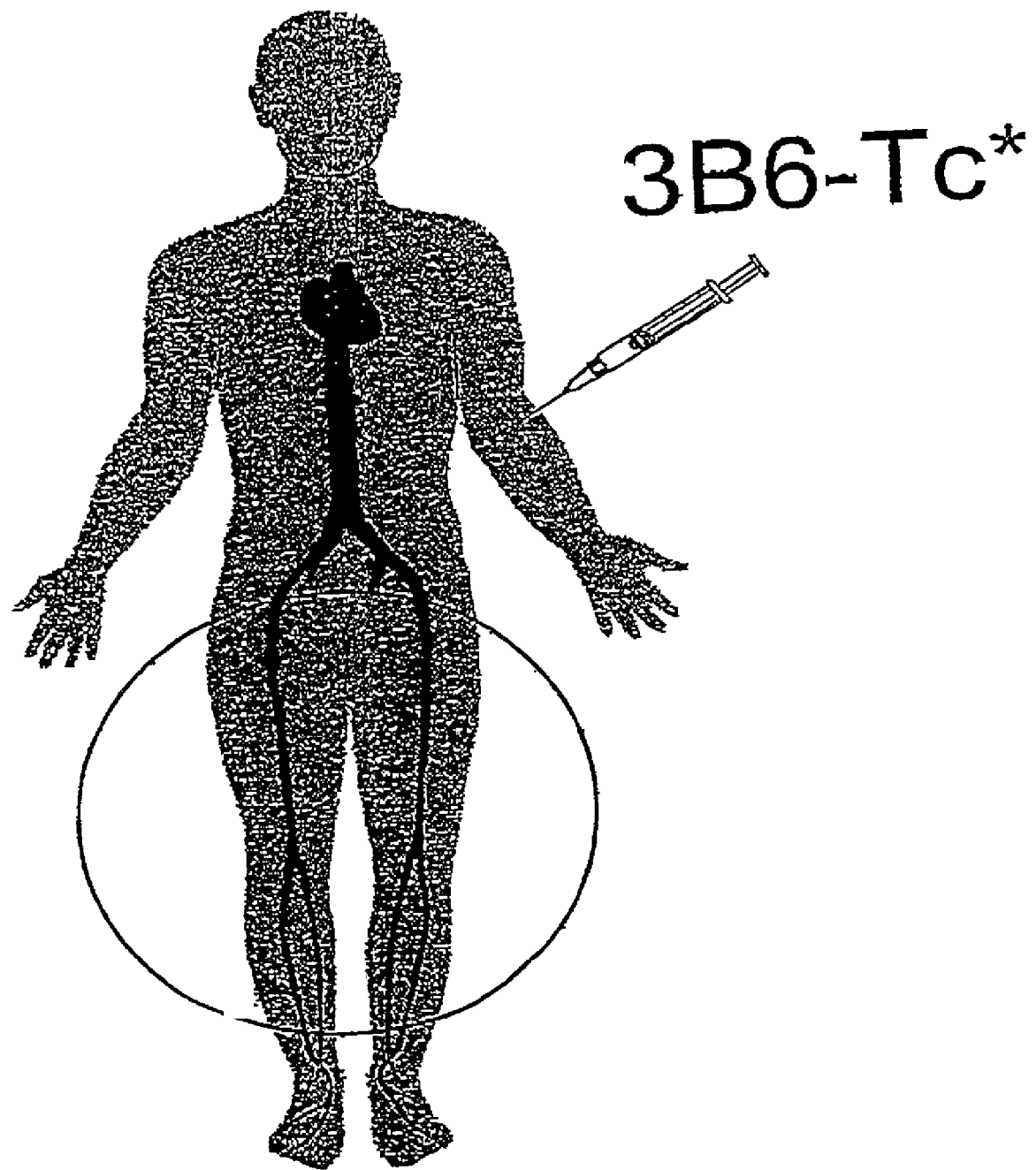
Figure 3B:
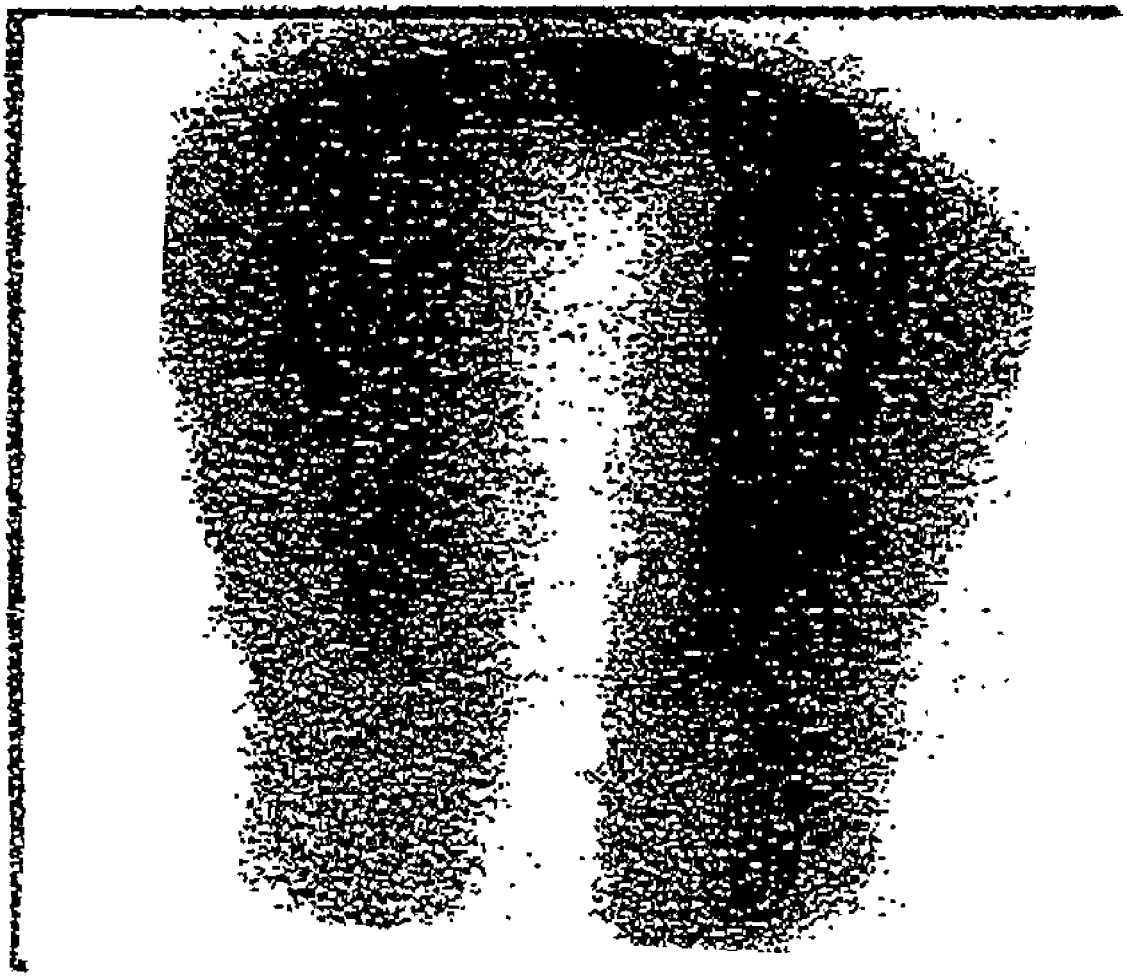

The 3B6 monoclonal antibody from mice and deimmunized form for humans is represented in FIG. 1A and exhibits specificity for fibrin which is a major part of blood clots (FIG. 1B). A clot imaging concept is developed by labelling the 3B6 monoclonal antibody with a nuclear tag, in this case, $^{99m}$Tc (FIG. 2). Administration of the labeled 3B6 deimmunized monoclonal antibody in humans FIG. 3A). Visualization of clots in the circulatory system such as blood clots in the anterior thighs (FIG. 3B) occurs by binding of the monoclonal antibody to fibrin resulting in concentration of radiation at the clot site.

EXAMPLE 10

Thromboviewing using 3B6-$^{99m}$TC

Pulmonary emboli (0.1–0.5 g) were created in anesthetized dogs by embolization of pre-formed thrombin made by infusion of thrombin and human fibrinogen through balloon catheters placed in the femoral veins. Purified Fab' fragments (0.35 mg) of a chimeric (human/murine) derivative of a fibrin-specific monoclonal antibody were labeled with a 15 mCi of $^{99m}$Tc. One hour after embolization, the radiolabeled antibody preparation was injected through a peripheral intravenous catheter. Eight hours after antibody injection, imaging scans were performed to visualize the emboli.

$^{99m}$Tc labeled antibody fragments cleared from the circulation with a $t_{1/2}$ of one hour for both subjects. In subject 1, two small emboli in the right lower lobe (combined mass, 0.187 g) were visible. The clot/blood radioactivity ratio was 38:1. In subject 2, one embolus in the right lower lobe (mass, 0.449 g) was visible. Clot/blood radioactivity ratio was 27:2. A small embolus (0.091 g) was discovered in the right ventricle of subject 1. The clot/blood radioactivity ratio was 45:1. No adverse effects were noted from either antibody administration or scanning methodology.

Infusion of radiolabeled anti-fibrin antibody fragments followed by imaging producesimages of emboli, even relatively small emboli in the periphery of the lung. The images are reliable and require minimal training to interpret. The technique can be used to image deep vein thrombin in the same setting. This agent is well tolerated by the subjects. There is no need for breath-holding or cardiac gating. It uses no nephrotoxic intravenous contrast dye. The radiation dose is similar to the dose used for ventilation/perfusion scans. This technology may simplify and clarify the diagnosis of PE and DVT, using technology available in most medical centres.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

All publications, patents, patent applications and provisional applications referred to herein are incorporated herein by reference in their entirety.

BIBLIOGRAPHY

Adams et al., *Cancer Res.* 53: 4026–4034, 1993.
Altschul et al., *Nucl. Acids Res.* 25:3389–3402. 1997.
Ausubel et al., "Current Protocols in Molecular Biology" John Wiley & Sons Inc, 1994–1998, Chapter 15.
Budzynski et al., *Blood* 54(4), 1979.
Carr et al. (International Patent Publication No. WO 98/52976).
Chothia et al., *J. Mol. Biol.* 196: 901, 1987.
Chothia et al., *J. Mol. Biol.* 227: 799, 1992.
Chou et al. (U.S. Pat. No. 6,056,957).
Coligan et al., *Current Protocols in Immunology*, John Wiley & Sons, Inc., 1991–1997.
Cumber et al., *J. Immunol.* 149: 120–126, 1992.
Daugherty et al., *Nucleic Acids Research* 19: 2471–2476, 1991.
Davies & Riechmann, *FEBS Lett.* 339: 285–290, 1994.
European Patent Publication No. 0 239 400.
Gefter et al., *Somatic Cell Genet.* 3: 231–236, 1977.
Glockshuber et al., *Biochem.* 29: 1363–1367, 1990.
Graeff and Halfer, "Detection and Relevance of Cross-linked Fibrin Derivatives in Blood", *Seminars in Thrombosis and Hemostatis* 8(1), 1982.
Hamers-Casterman et al., *Nature* 363: 446–448, 1993.
Jones et al., *Nature* 321: 522–525, 1986.
Kabat et al., "Sequences of Proteins of Immunological Interest", U.S. Department of Health and Human Services, 1983.
Kennet et al. (eds) *Monoclonal Antibodies and Hybridomas: A New Dimension in Biological Analyses*, pp. 376–384, Plenum Press, New York, 1980.
Kohler and Milstein, *Eur. J. Immunol.* 6(7): 511–519, 1976.
Kohler and Milstein, *Nature* 256: 495–499, 1975.
Kostelny et al., *J. Immunol.* 148: 1547–1553, 1992.
Kozbor et al., *Methods in Enzymology* 121: 140, 1986.
Krebber et al., *J. Immunol. Methods* 201(1): 35–55, 1997.
Ku & Schutz, *Proc. Natl. Acad. Sci. USA* 92: 6552–6556, 1995.
Liu et al., *Proc. Natl. Acad. Sci. USA* 84: 3439–3443, 1987.
Morgan et al. (U.S. Pat. No. 6,180,377).

Orlandi et al., *Proc. Natl. Acad. Sci. USA* 86: 3833–3837, 1989.
Plückthun et al., *In Antibody engineering: A practical approach* 203–252, 1996.
Plünckthun, *Biochem.* 31: 1579–1584, 1992.
Queen et al. (U.S. Pat. No. 6,180,370).
Reiter et al., *Biochem.* 33: 5451–5459, 1994.
Reiter et al., *Cancer Res.* 54: 2714–2718, 1994.
Reiter et al., *J. Biol. Chem.* 269: 18327–18331, 1994.
Riechmann et al., *Nature* 332: 323–327, 1988.
Shulman et al., *Nature* 276: 269–270, 1978;
Tempest et al., *Biotechnology* 9: 266–271, 1991.
Toyama et al., "i Monoclonal Antibody, Experiment Manual", published by Kodansha Scientific, 1987.
Trowbridge, *J. Exp. Med.* 148(1): 313–323, 1978.
Verhoeyen et al., *Science* 239: 1534–1536, 1988.
Volk et al., *J. Virol.* 42(1): 220–227, 1982.
Ward et al., *Nature* 341: 544–546, 1989.
Webber et al., *Mol. Immunol.* 32: 249–258, 1995.
Wilner et al., *Biochemistry* 21: 2687–2692, 1982.
Winter and Milstein, *Nature* 349: 293, 1991,

---

The invention claimed is:

1. A deimmunized antibody or antibody fragment thereof specific for an epitope on human D-dimer which recognizes cross-linked fibrin but not fibrinogen, wherein said antibody or antibody fragment thereof comprises a combination of an H and an L chain v-domain comprising a combination of amino acid sequences selected from the group consisting of SEQ ID NO:1/SEQ ID NO:4, SEQ ID NO:2/SEQ ID NO:4, SEQ ID NO:3/SEQ ID NO:4, SEQ ID NO:1/SEQ ID NO:6, SEQ ID NO:2/SEQ ID No:6, SEQ ID NO:2/SEQ ID NO:5, SEQ ID NO:3/SEQ ID NO:5, SEQ ID NO:3/SEQ ID NO:6, and SEQ ID NO:1/SEQ ID NO:5.

2. The antibody or antibody fragment thereof of claim 1 wherein said antibodyfragment is an Fab' fragment.

3. A conjugate comprising a deimmunized antibody or antibody fragment according to claim 1, and an imaging tag selected from the group consisting of $^{99m}$Tc, $^{18}$F, $^{64}$Cu, $^{67}$Ga, $^{68}$Ga, $^{77}$Br, $^{97}$Ru, $^{111}$In, $^{123}$I, $^{124}$I, $^{131}$I and $^{188}$Re.

4. A conjugate comprising a deimmunized antibody fragment according to claim 2, and an imaging tag selected from the group consisting of $^{99m}$Tc, $^{18}$F, $^{64}$Cu, $^{67}$Ga, $^{68}$Ga, $^{77}$Br, $^{97}$Ru, $^{111}$In, $^{123}$I, $^{124}$I, $^{131}$I and $^{188}$Re.

5. The conjugate of claim 3 wherein the imaging tag is $^{99m}$Tc.

6. The conjugate of claim 4 wherein the imaging tag is $^{99m}$Tc.

7. A conjugate comprising an imaging tag and an antibody or antibody fragment thereof according to claim 1.

8. The conjugate of claim 7 wherein said imaging tag is an x-ray, MRI, ultrasound-type tag or CT-type tag.

* * * * *